US007670591B2

(12) United States Patent  
Malmstrom et al.

(10) Patent No.: US 7,670,591 B2
(45) Date of Patent: Mar. 2, 2010

(54) HETEROARYL SUBSTITUTED BENZOXAZOLES

(75) Inventors: Jonas Malmstrom, Sodertalje (SE); David Pyring, Sodertalje (SE); Can Slivo, Sodertalje (SE); Daniel Sohn, Sodertalje (SE); Britt-Marie Swahn, Sodertalje (SE); David Wensbo, Grodinge (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/763,151

(22) Filed: Jun. 14, 2007

(65) Prior Publication Data

US 2008/0027051 A1 Jan. 31, 2008

Related U.S. Application Data

(60) Provisional application No. 60/814,936, filed on Jun. 19, 2006.

(51) Int. Cl.
 A61K 51/04 (2006.01)
 A61K 31/443 (2006.01)
 C07D 413/04 (2006.01)
(52) U.S. Cl. .................... 424/1.81; 514/338; 546/271.7
(58) Field of Classification Search .............. 514/233.8, 514/275, 338, 375; 544/124, 297; 546/271.7; 548/217; 424/1.81
See application file for complete search history.

(56) References Cited

U.S. PATENT DOCUMENTS

| 4,232,010 | A | | 11/1980 | Tsukamoto et al. |
| 5,236,619 | A | | 8/1993 | Iwaki et al. |
| 5,518,713 | A | * | 5/1996 | Raspanti ...................... 424/59 |
| 2005/0101647 | A1 | * | 5/2005 | Oda et al. ................... 514/367 |
| 2007/0258887 | A1 | | 11/2007 | Tamagnan et al. |

FOREIGN PATENT DOCUMENTS

| EP | 120589 B1 | 6/1988 |
| EP | 1612204 A1 | 1/2006 |
| JP | 2004250411 | 9/2004 |
| JP | 11116476 A | 5/2008 |
| WO | 9517095 A1 | 6/1995 |
| WO | 0216333 A2 | 2/2002 |
| WO | 02051821 A1 | 7/2002 |
| WO | 02085903 A2 | 10/2002 |
| WO | 02/092086 A1 | 11/2002 |
| WO | 03051859 A1 | 6/2003 |
| WO | 03/106439 A1 | 12/2003 |
| WO | 2004/008319 A2 | 1/2004 |
| WO | 2004012736 A1 | 2/2004 |
| WO | 2004083195 A1 | 9/2004 |
| WO | 2004101558 A1 | 11/2004 |
| WO | 2006014381 A2 | 2/2006 |
| WO | 2006030032 A2 | 3/2006 |
| WO | 2006125324 A1 | 11/2006 |
| WO | 2007/033080 A2 | 3/2007 |
| WO | 2007/035405 A2 | 3/2007 |
| WO | 2007/047204 A1 | 4/2007 |
| WO | 2007/063946 A1 | 6/2007 |
| WO | 2007/086800 A1 | 8/2007 |
| WO | 2008091195 A1 | 7/2008 |

OTHER PUBLICATIONS

Vippagunta et al., Crystalline solids, 2001, Advanced Drug Delivery Reviews, 48, pp. 3 and 18.*
Zhuang, Zhi-Ping; et al., "IBOX(2-(4'-dimethylaminophenyl)-6-iodobenzoxazole): a ligand for imaging amyloid plaques in the brain." Nuclear Medicine and Biology (2001), 28(8), 887-894, CODEN: NMBIEO; ISSN: 0969-8051.
Thakak, K. A. et al., "Reaction of guanidine with 3-formylchromones." Journal of the Indian Chemical Society (1984), 61 (6), 550-2, CODEN: JICSAH; ISSN: 0019-4522.
Hardy, J. and Selkoe, D.J., "The Amyloid Hypothesis of Alzheimer's Disease: Progress and Problems on the Road to Therapeutics." Science, vol. 297, pp. 353-356, 2002.
Mathis, C.A. et al., "Synthesis and Evaluation of 11C-Labeled 6-Substituted 2-Arylbenzothiazoles as Amyloid Imaging Agents." J. Med. Chem. 2003, 46, pp. 2740-2754.
Klunk, W.E. et al., "Imaging Brain Amyloid in Alzheimer's Disease with Pittsburgh Compound-B." Ann Neurol. 2004, 55, pp. 306-319.
Ono, M. et al., "Synthesis and biological evaluation of (E)-3-styrylpyridine derivatives as amyloid imaging agents for Alzheimer's disease." Nuclear Medicine and Biology, 2005, vol. 32, pp. 329-335.

(Continued)

Primary Examiner—Kamal A Saeed
Assistant Examiner—Kristin Bianchi
(74) Attorney, Agent, or Firm—David M. Gryte

(57) ABSTRACT

The present invention relates to novel heteroaryl substituted benzoxazole derivatives and therapeutic uses for such compounds, having the structural formula (Ia) below:

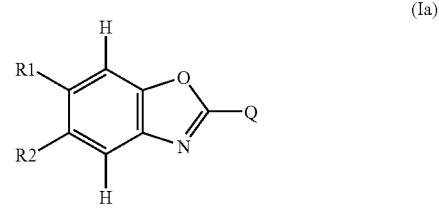

(Ia)

Figure 1:
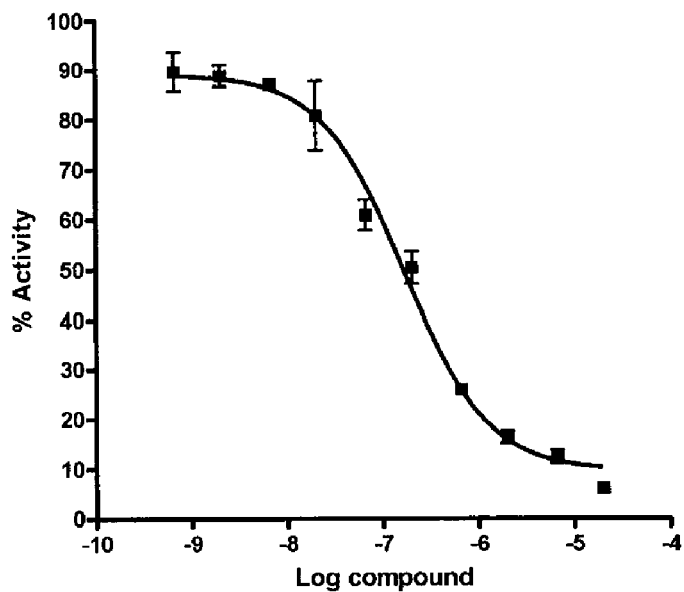

and to their pharmaceutically acceptable salt, compositions and methods of use. Furthermore, the invention relates to novel heteroaryl substituted benzoxazole derivatives that are suitable for imaging amyloid deposits in living patients, their compositions, methods of use and processes to make such compounds. More specifically, the present invention relates to a method of imaging amyloid deposits in brain in vivo to allow antemortem diagnosis of Alzheimer's disease as well as measuring clinical efficacy of Alzheimer's disease therapeutic agents.

31 Claims, 3 Drawing Sheets

OTHER PUBLICATIONS

Zhang, W. et al., "18F-labeled styrylpyridines as PET agents for amyloid plaque imaging." Nuclear Medicine and Biology, 2007, vol. 34, pp. 89-97.
English Abstract for JP 2004-250411.
Allsop et al., "3-p-Toluoyl-2-[4'-(3-diethylaminopropoxy)-phenyl]-benzofuran and 2-[4'-(3-Diethylaminopropoxy)-phenyl]-benzofuran Do Not Act as Surfactants or Micelles when Inhibiting the Aggregation of β-Amyloid Peptide", Bioorg. Med.Chem.Lett, 2001, 255-257, 11(2).
Barni, et al., "2-(Methylpyridyl or quinolyl)benz-X-azoles, Salts and Polymethine Dyes (1)", Journal of Heterocyclic Chemistry, 1979, P1579-82, 16(8).
Cai et al., "Synthesis an Evaluation of Two 18F-Labeled 6-Iodo (4-N,N-dimethylamino)phenylimidazo [1,2-a] pyridine Derivatives as Prospective Radioligands for β-Amyloid in Alzheimer's Disease", J.Med.Chem, 2004, 2208-2218, 47(9).
Chang et al., "Synthesis and evaluation of benzothiophene derivatives as ligands for imagining β-amyloid plaques in Alzheimer's disease", Nuclear Medicine and Biology, 2006, 811-820, 33.
Choi at al., "Synthesis of 2-(4-Hydroxyphenyl)benzofurans and Their Application to b-Amyloid Aggregation Inhibitor", Archives of Pharmacal Research, 2004, 19-24, 27(1).
Coimbra et al., "The Role of MRI and PET/SPECT in Alzheimer's Disease", Curr.Top.Med.Chem, 2006, 629-647, vol. 6.
Guram et al., "New Catalysts for Suzuki-Miyaura Coupling Reactions of Heteroactom-Substituted Heteroaryl Chlorides", J. Org. Chem. 2007, p. 5104-5112, vol. 72.
Hardy et al., "The Amyloid Hypothesis of Alzheimer's Disease: Progress and Problems on the Road to Therapeutics", J. Science, 2002, 353-356, 297.
Howlett et al., "Inhibition of fibril formation in β-amyloid peptide by a novel series of benzofurans", Biochemical Journal, 1999, 283-289, 340(1).
Klunk et al., "Imaging Brain Amyloid in Alzheimer's Disease with Pittsburg Compound-B", Ann Neurol, 2004, 306-319, 55.
Kung et al., "IMPY: an improved thioflavin-T derivative for in vivo labeling of β-amyloid plaques", Brain Research, 2002, 202-210, 956.
Kung et al., "Binding of two potential imaging agents targeting amyloid plaques in postmortem brain tissues of patients with Alzheimer's disease", Brain Research, 2004, 98-105, 1025(1-2).
Kung et al., Erratum to "Binding of two potential imaging agents targeting amyloid plaques in postmortem brain tissues of patients with Alzheimer's disease", Brain Research, 2005, 302, 1031 (2).
Lockhart et al., "Evidence of the Presence of Three Distint Binding Sites for the Thioflavin T Class of Alzheimer's Disease PET Imaging Agents on β-Amyloid Peptide Fibrils", J Biol.Chem., 2005, 7677-7684, 280(9).
Lu, et al., "Synthesis and biodistribution of [131I]IMPY", Nuclear Science and Techniques, 2005, 289-292, 16(5).
Mathis et al., "Synthesis and Evaluation of 11C-Labeled 6-Substituted 2-Arylbenzothiazoles as Amyloid Imaging Agents", Med Chem., 2003, 2740-2754, 46.
Miller, "A Better View of Brain Disorders", Science, 2006, 1376, 313.
Newberg et al., Safety, Biodistribution, and Dosimetry of 123I-IMPY: A Novel Amyloid Plaque-Imaging Agent for the Diagnosis of Alzheimer's Disease, Journal of Nuclear Medicine, 2006, 748-754, 47(5).
Nordberg, A. "PET imaging of amyloid in Alzheimer's disease", Lancet, Neurol., 2004, 519-527, 3.
Ono et al., Benzofuran derivatives as Aβ-aggregate-specific imaging agents for Alzheimer's disease, Nuclear Med. Biol., 2002, 633-642, 29(6).
Ono et al., "Synthesis and biological evaluation of (E)-3-styrylpyridine derivatives as amyloid imaging agents for Alzheimer's disease", Nuclear Medicine and Biology, 2005, 329-335, 32.
Ono et al., "Novel Benzofuran Derivatives for PET Imaging of β-Amyloid Plaques in Alzheimer's Disease Brains", J. Med. Chem., 2006, 2725-2730, 49.
Shi et al., "Antitumor Benzothiazoles. 3.1 Synthesis of 2-(4-Aminophenyl) benzothiazoles and Evaluation of Their Activities against Breast Cancer Cell Lines in Vitro and in Vivo", Journal of Medicinal Chemistry, 1996, 3375-3384, 39(17).
Shoghi-Jadid et al., "Localization of Neurofibrillary Tangles and Beta-Amyloid Plaques in the Brains of Living Patients With Alzheimer Disease",The American Journal of Geriatric Psychiatry, 2002, 24-35,10.
Thakak et al., "Reaction of guanidine with 3-formylchromones", Journal of the Indian Chemical Society, 1984, 550-2, 61(6): JICSAH;ISSN: 0019-4522.
Twyman et al., "A Short Synthesis of the β-amyloid (Aβ) Aggregation Inhibitor 3-p-Toluoyl-2-[4'-(3-diethylaminopropoxy)-phenyl]-benzofuran", Tetrahedron Lett, 1999, 9383-9384, 40(52).
Zeng et al. "Synthesis and evaluation of two 18F-labeled imidazol [1,2-a]pyridine analogues as potential agents for imaging β-amyloid in Alzheimer's disease", Bioorganic & Medicinal Chemistry Letters, 2006, 3015-3018, 16(11).
Zhang et al., "F-18 Stilbenes as PET Imaging Agents for Detecting β-Amyloid Plaques in the Brain", J.Med. Chem., 2005, 5980-5988, 48.
Zhang et al., "18F-labeled styrylpyridines as PET agents for amyloid plaque imaging", Nuclear Medicine and Biology, 2007, 89-97, 34.
Zhuang et al., "IBOX (2-(4'-dimethylaminophenyl)-6-iodobenzoxazole) : a ligand for imaging amyloid plaques in the brain", Nuclear Medicine and Biology, 2002, 887-894, 28(8), CODEN:NMBIEO;ISSN:0969-8051.
Zhuang et al., "Structure-Activity Relationship of Imidazo[1,2-a]pyridines as Ligands for Detecting β-Amyloid Plaques in the Brain", Journal of Medicinal Chemistry, 2003, 237-243, 46(2).
English abstract for JP11116476, Apr. 27, 1999.
Vippagunta et al., Crystalline Solids:, 2001, Advanced Drug Delivery Reviews, 48, pp. 3 and 18.
STN International, File Caplus, Caplus accession No. 1988:580390, document No. 109:180390, Shiino, Yasuko et al., "Electrophotographic charge-generating disazo photoconductors", & JP, A, 63094248, 19880425.
STN International, File HCaplus, HCaplus accession No. 1999:476741, Document No. 131:228612, Benhida, Rachid et al:"Synthesis of 6-allyl—and 6-heteroarylindoles by palladium catalyzed stille cross-coupling reaction", &Tetrahedron Letters (1999), 40(31), 5701-5703.
158229 Caplus, AN 2002:293449, DN 136:319426, Apr. 18, 2002.
STN International, File Caplus, Caplus accession No. 2003:60939, document No. 138:287190, Soares-Santos, P.C.R. et al., "Blue-emitting flurophores based on 1,3-benzoxazolyl and 1,3-benzothiazolyl-substituted indoles and carbazoles", & Advances in Colour Science and Technology (2002), 5(4), 94-98.
International Search Report for International application No. PCT/SE2007/000591, Nov. 6, 2007.
Swedish Patent Office Search Report dated Jan. 3, 2007.

\* cited by examiner

HETEROARYL SUBSTITUTED BENZOXAZOLES

The present invention relates to novel heteroaryl substituted benzoxazole derivatives and therapeutic uses for such compounds. Furthermore, the invention relates to novel heteroaryl substituted benzoxazole derivatives that are suitable for imaging amyloid deposits in living patients, their compositions, methods of use and processes to make such compounds. More specifically, the present invention relates to a method of imaging amyloid deposits in brain in vivo to allow antemortem diagnosis of Alzheimer's disease as well as measuring clinical efficacy of Alzheimer's disease therapeutic agents.

BACKGROUND OF THE INVENTION

Amyloidosis is a progressive, incurable metabolic disease of unknown cause characterized by abnormal deposits of protein in one or more organs or body systems. Amyloid proteins are manufactured, for example, by malfunctioning bone marrow. Amyloidosis, which occurs when accumulated amyloid deposits impair normal body function, can cause organ failure or death. It is a rare disease, occurring in about eight of every 1,000,000 people. It affects males and females equally and usually develops after the age of 40. At least 15 types of amyloidosis have been identified. Each one is associated with deposits of a different kind of protein.

The major forms of amyloidosis are primary systemic, secondary, and familial or hereditary amyloidosis. There is also another form of amyloidosis associated with Alzheimer's disease. Primary systemic amyloidosis usually develops between the ages of 50 and 60. With about 2,000 new cases diagnosed annually, primary systemic amyloidosis is the most common form of this disease in the United States. Also known as light-chain-related amyloidosis, it may also occur in association with multiple myeloma (bone marrow cancer). Secondary amyloidosis is a result of chronic infection or inflammatory disease. It is often associated with Familial Mediterranean fever (a bacterial infection characterized by chills, weakness, headache, and recurring fever), Granulomatous ileitis (inflammation of the small intestine), Hodgkin's disease, Leprosy, Osteomyelitis and Rheumatoid arthritis.

Familial or hereditary amyloidosis is the only inherited form of the disease. It occurs in members of most ethnic groups, and each family has a distinctive pattern of symptoms and organ involvement. Hereditary amyloidosis is thought to be autosomal dominant, which means that only one copy of the defective gene is necessary to cause the disease. A child of a parent with familial amyloidosis has a 50-50 chance of developing the disease.

Amyloidosis can involve any organ or system in the body. The heart, kidneys, gastrointestinal system, and nervous system are affected most often. Other common sites of amyloid accumulation include the brain, joints, liver, spleen, pancreas, respiratory system, and skin.

Alzheimer's disease (AD) is the most common form of dementia, a neurologic disease characterized by loss of mental ability severe enough to interfere with normal activities of daily living, lasting at least six months, and not present from birth. AD usually occurs in old age, and is marked by a decline in cognitive functions such as remembering, reasoning, and planning.

Between two and four million Americans have AD; that number is expected to grow to as many as 14 million by the middle of the 21st century as the population as a whole ages. While a small number of people in their 40 s and 50 s develop the disease, AD predominantly affects the elderly. AD affects about 3% of all people between ages 65 and 74, about 20% of those between 75 and 84, and about 50% of those over 85. Slightly more women than men are affected with AD, even when considering women tend to live longer, and so there is a higher proportion of women in the most affected age groups.

The accumulation of amyloid Aβ-peptide in the brain is a pathological hallmark of all forms of AD. It is generally accepted that deposition of cerebral amyloid Aβ-peptide is the primary influence driving AD pathogenesis. (Hardy J and Selkoe D. J., Science. 297: 353-356, 2002).

Imaging techniques, such as positron emission tomography (PET) and single photon emission computed tomography (SPECT), are effective in monitoring the accumulation of amyloid deposits in the brain and correlating it to the progression of AD. The application of these techniques requires the development of radioligands that readily enter the brain and selectively bind to amyloid deposits in vivo.

A need exists for amyloid binding compounds that can cross the blood-brain barrier, and consequently, can be used in diagnostics. Furthermore, it is important to be able to monitor the efficacy of the treatment given to AD patients, by measuring the effect of said treatment by measuring changes of AD plaque level.

Properties of particular interest of a detectable amyloid-binding compound, besides high affinity for amyloid deposits in vivo and high and rapid brain entrance, include low unspecific binding to normal tissue and rapid clearance from the same. These properties are commonly dependant on the lipophilicity of the compound. TZDM is a benzothiazole compound considered to be non-ideal for imaging of amyloid deposits in vivo due to its high unspecific binding to normal tissue. The corresponding benzoxazole analog, IBOX, has relatively higher brain entrance, and relatively more rapid clearance from normal brain tissue, and thus constitutes thus an improvement over TZDM (Zhuang et al. Nucl. Med. Biol. 2001, 28, 887). Based partly on the relatively higher clearance from normal brain tissue as compared to related analogues, [$^{11}$C]PIB was selected from amongst these for further evaluations in human subjects (Mathis et al. J. Med. Chem. 2003, 46, 2740). Subsequently, a study on the use of [$^{11}$C]PIB for the detection of amyloid deposits in-vivo in the human by the PET-technique was conducted (Klunk et al. Ann Neurol. 2004, 55, 306). In this study, significant higher retention of [$^{11}$C]PIB in relevant regions of the brain, was observed in subjects with diagnosed AD as compared to healthy controls. Related methods and derivatives are described in WO 2002/16333 and WO 2004/08319.

There is a need for improved compounds in order to obtain a signal-to-noise ratio high enough to allow detailed detection of amyloid deposits throughout all brain regions, and providing improved reliability in quantitative studies on amyloid plaque load in relation to drug treatments.

The present invention provides heteroaryl substituted benzoxazole derivatives carrying such unexpected improvements over known benzoxazole derivatives providing inter alia advantageously associated low unspecific binding and rapid brain clearance.

SHORT DESCRIPTION OF DRAWINGS

FIG. 1. Competition binding: Activity ("% Activity") of remaining [$^3$H]PIB versus increasing concentration of non-labeled compounds ("log compound") of the present invention. Compound 2-[6-(methylamino)pyridin-3-yl]-1,3-benzooxazol-6-ol shown in the competition binding assay.

Figure 2:
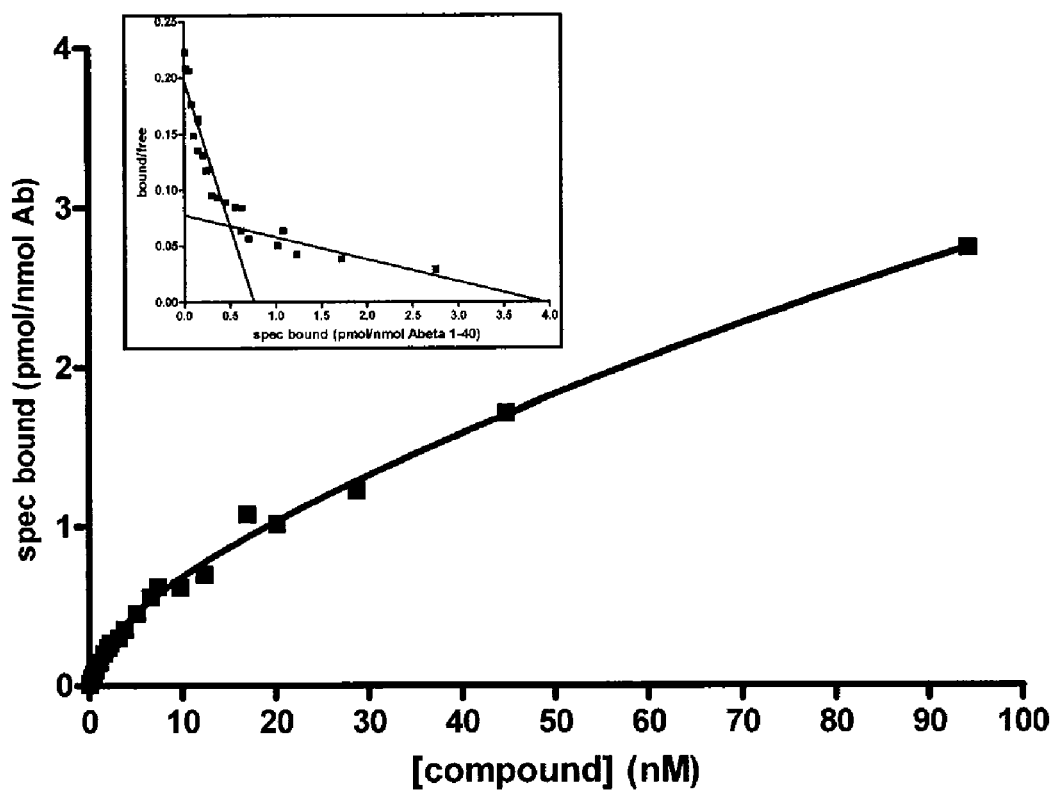

FIG. 2. Saturation binding: Example of a saturation experiment: Increasing concentration of compound specifically bound to synthetic Aβ1-40 fibrils. Compound [N-methyl-$^3$H$_3$]-2-(6-methylamino-pyridin-3-yl)-benzooxazol-6-ol shown in the saturation experiment. Inserted: a scatchard plot of the same experiment.

Figure 3:
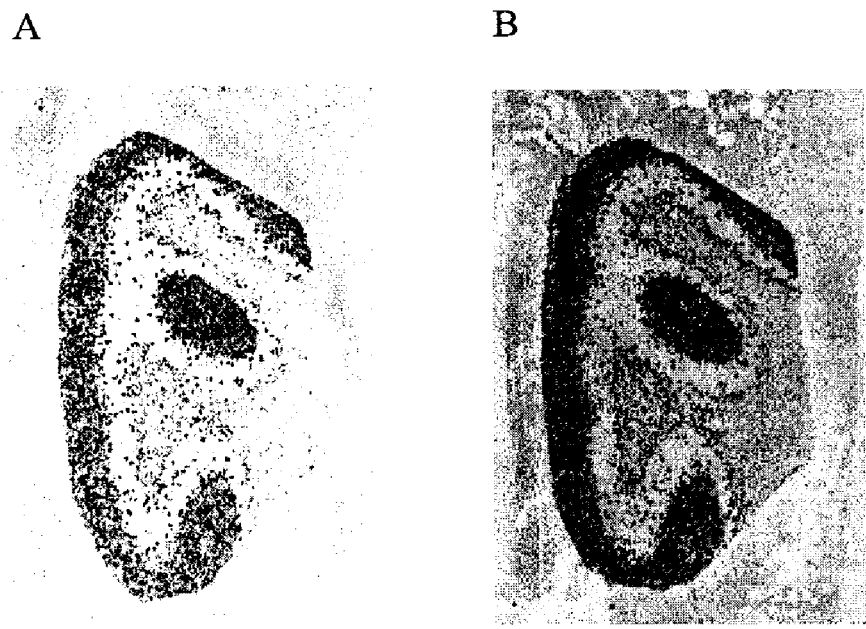

FIG. 3. Binding to amyloid plaques in post-mortem human AD brains: Example of amyloid binding post mortem in human brain tissue section using (A) 10 nM of [N-methyl-$^3$H$_3$]-2-(6-methylamino-pyridin-3-yl)-benzooxazol-6-ol or (B) 10 nM of [$^3$H]—BO.

Figure 4:
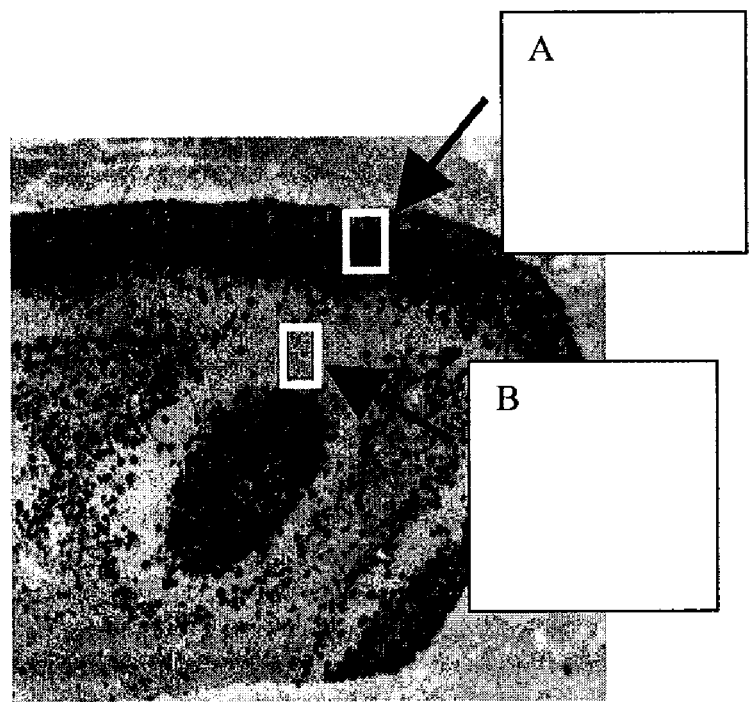

FIG. 4. Quantitative comparison of nonspecific amyloid binding: Image illustrating outlined areas for measurement of binding density in gray matter with amyloid plaques, and white matter area with no amyloid plaques.

Figure 5:
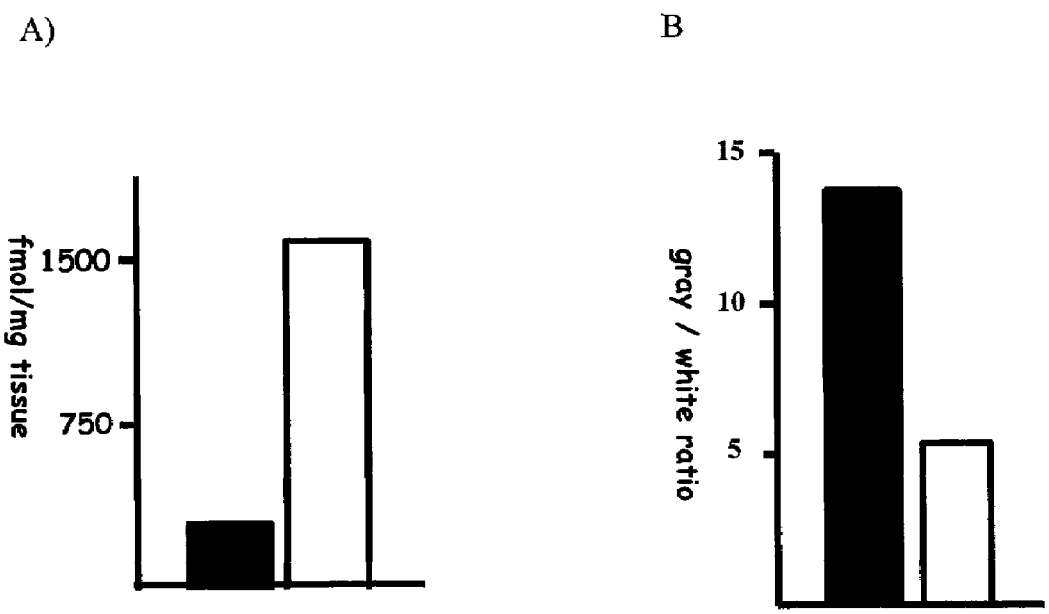

FIG. 5. Quantitative comparison of nonspecific amyloid binding in post mortem human brain tissue section using compound [N-methyl-$^3$H$_3$]-2-(6-methylamino-pyridin-3-yl)-benzooxazol-6-ol, and compound [$^3$H]—BO. (A) Bar graphs showing amount of unspecific binding (white matter region) for 10 nM of compound [N-methyl-$^3$H$_3$]-2-(6-methylamino-pyridin-3-yl)-benzooxazol-6-ol (black bar) and 10 nM of compound [$^3$H]—BO (white bar). (B) Bar graphs showing ratio between gray matter binding and white matter binding for 10 nM of compound [N-methyl-$^3$H$_3$]-2-(6-methylamino-pyridin-3-yl)-benzooxazol-6-ol (black bar) and 10 nM of compound [$^3$H]—BO (white bar) as an indication of signal to background ratio.

Figure 6:
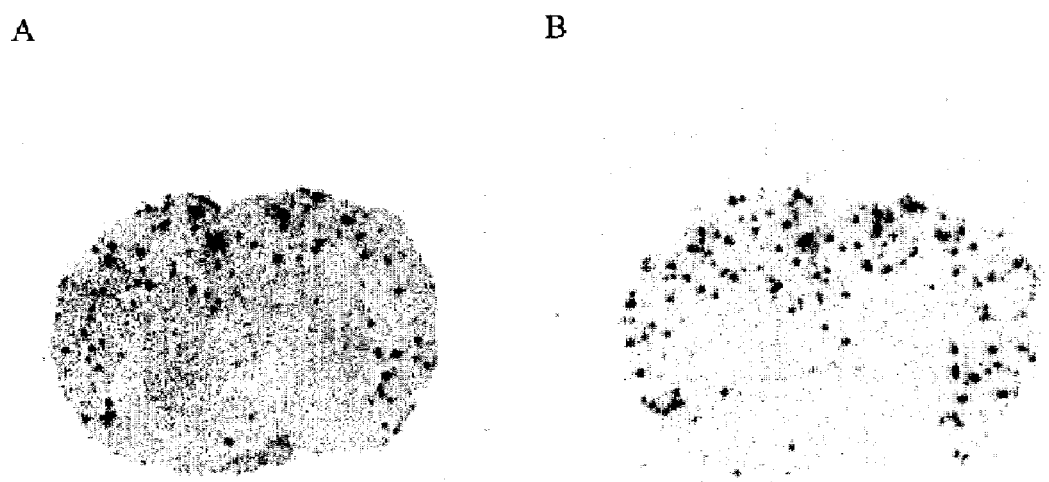

FIG. 6. Binding in transgenic (APP/PS1) mouse brain after compound administration in-vivo: Autoradiograms illustrating labeling after in vivo administration (1 mCi i.v.) of a tritium labeled compound of the present invention compound [N-methyl-$^3$H$_3$]-2-(6-methylamino-pyridin-3-yl)-benzooxazol-6-ol in brain sections from APP/PS1 double transgenic mice. The brain sections were either exposed unrinsed (A) or rinsed in Trizma-base® buffer (pH 7.4) (B).

DISCLOSURE OF THE INVENTION

The present invention provides methods for measuring effects of compounds or treatments that exerts an influence on AD plaques, directly or indirectly, by measuring changes of AD plaque level.

In a first aspect of the invention, there is provided compounds according to formula Ia

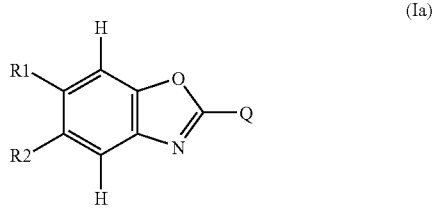

(Ia)

wherein

R1 is selected from hydrogen, halo, $C_{1-6}$ alkyl, $C_{1-6}$ fluoroalkyl, $C_{1-3}$ alkyleneOC$_{1-3}$ alkyl, $C_{1-3}$ alkyleneOC$_{1-3}$ fluorolkyl, $C_{1-3}$ alkyleneNH$_2$, $C_{1-3}$ alkyleneNHC$_{1-3}$ alkyl, $C_{1-3}$ alkyleoeN(C$_{1-3}$ alkyl)$_2$, $C_{1-3}$ alkyleneNHC$_{1-3}$ fluoroalkyl, $C_{1-3}$ alkyleneN(C$_{1-3}$ fluoroalkyl)$_2$, $C_{1-3}$ alkyleneN(C$_{1-3}$ alkyl)C$_{1-3}$ fluoroalkyl, hydroxy, $C_{1-6}$ alkoxy, $C_{1-6}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(CO)C$_{1-3}$ alkyl, NH(CO)C$_{1-3}$ fluoroalkyl, NH(CO)C$_{1-3}$ alkoxy, NH(CO)C$_{1-3}$ fluoroalkoxy, NHSO$_2$C$_{1-3}$ alkyl, NHSO$_2$C$_{1-3}$ fluoroalkyl, (CO)C$_{1-3}$ alkyl, (CO)C$_{1-3}$ fluoroalkyl, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene), nitro and cyano;

R2 is selected from hydrogen, fluoro, bromo, iodo, $C_{1-6}$ alkyl, $C_{1-6}$ fluoroalkyl, $C_{1-3}$ alkyleneOC$_{1-3}$ alkyl, $C_{1-3}$ alkyleneOC$_{1-3}$ fluorolkyl, $C_{1-3}$ alkyleneNH$_2$, $C_{1-3}$ alkyleneNHC$_{1-3}$ alkyl, $C_{1-3}$ alkyleneN(C$_{1-3}$ alkyl)$_2$, $C_{1-3}$ alkyleneNHC$_{1-3}$ fluoroalkyl, $C_{1-3}$ alkyleneN(C$_{1-3}$ fluoroalkyl)$_2$, $C_{1-3}$ alkyleneN(C$_{1-3}$ alkyl)C$_{1-3}$ fluoroalkyl, hydroxy, $C_{1-6}$ alkoxy, $C_{1-6}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(CO)C$_{1-3}$ alkyl, NH(CO)C$_{1-3}$ fluoroalkyl, NH(CO)C$_{1-3}$ alkoxy, NH(CO)C$_{1-3}$ fluoroalkoxy, NHSO$_2$C$_{1-3}$ alkyl, NHSO$_2$C$_{1-3}$ fluoroalkyl, (CO)C$_{1-3}$ alkyl, (CO)C$_{1-3}$ fluoroalkyl, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene) and cyano;

Q is a nitrogen-containing aromatic heterocycle selected from Q1 to Q5;

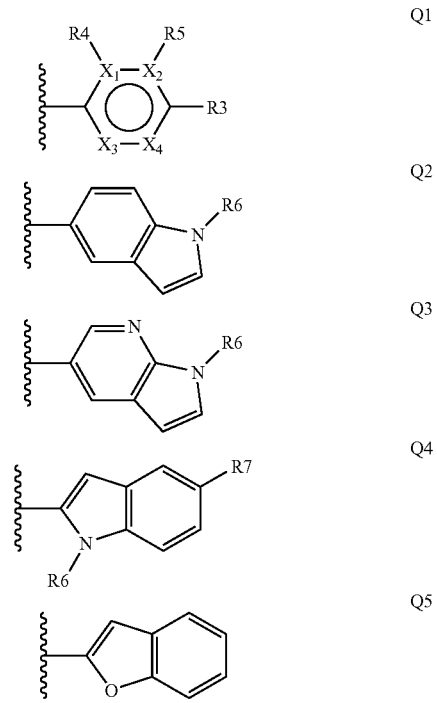

wherein

Q1 is a 6-membered aromatic heterocycle containing one or two N atoms, wherein $X_1$, $X_2$, $X_3$ and $X_4$ are independently selected from N or C; and wherein one or two of $X_1$, $X_2$, $X_3$ and $X_4$ is N and the remaining is C, and wherein when the atom $X_1$ is C, said C is optionally substituted with R4; and wherein when the atom $X_2$ is C, said C is optionally substituted with R5;

R3 is selected from fluoro, bromo, iodo, $C_{1-4}$ alkyl, $C_{1-4}$ fluoroalkyl, $C_{1-3}$ alkyleneOC$_{1-3}$ alkyl, $C_{1-3}$ alkyleneOC$_{1-3}$ fluoroalkyl, $C_{1-3}$ alkyleneNH$_2$, $C_{1-3}$ alkyleneNHC$_{1-3}$ alkyl, $C_{1-3}$ alkyleneN(C$_{1-3}$ alkyl)$_2$, $C_{1-3}$ alkyleneNHC$_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-4}$ alkoxy, $C_{1-4}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH($C_{0-3}$ alkylene)G2, N($C_{0-1}$ alkyl)N($C_{0-1}$ alkyl)$_2$, N($C_{0-1}$ alkyl)O$C_{0-1}$ alkyl, N$C_{1-3}$ alkyl(CO)$C_{1-3}$ alkyl, NH(CO)$C_{1-3}$ alkyl, NH(CO)$C_{1-3}$ fluoroalkyl, NH(CO)G2, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), (CO)G2, (CO)NH$_2$G2, S$C_{1-3}$ alkyl, S$C_{1-3}$ fluoroalkyl, SO$_2$NH$_2$, SO$_2$NH$C_{1-3}$ alkyl, SO$_2$NH$C_{1-3}$ fluoroalkyl, SO$_2$N($C_{1-3}$ alkyl)$_2$, SO$_2$N($C_{1-3}$ fluoroalkyl)$_2$, SO$_2$N($C_{1-3}$ alkyl)$C_{1-3}$ fluoroalkyl, cyano and G1, wherein G1 is;

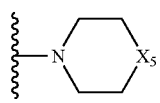
G1

$X_5$ is selected from O, NH, N$C_{1-3}$ alkyl and N$C_{1-3}$ fluoroalkyl;

G2 is phenyl or a 5- or 6-membered aromatic heterocycle and optionally substituted with a substituent from fluoro, bromo, iodo, methyl and methoxy;

R4 is selected from fluoro, bromo, iodo, $C_{1-4}$ alkyl, $C_{1-4}$ fluoroalkyl, $C_{1-4}$ alkoxy, $C_{1-4}$ fluoroalkoxy, amino, NH$C_{1-3}$ alkyl and NH$C_{1-3}$ fluoroalkyl;

R5 is selected from fluoro, bromo, iodo, $C_{1-4}$ alkyl, $C_{1-4}$ fluoroalkyl, $C_{1-4}$ alkoxy, $C_{1-4}$ fluoroalkoxy, amino, NH$C_{1-3}$ alkyl and NH$C_{1-3}$ fluoroalkyl;

R6 is selected from hydrogen, $C_{1-4}$ alkyl, $C_{1-4}$ fluoroalkyl and (CO)$C_{1-4}$alkoxy;

R7 is selected from hydrogen, fluoro, bromo, iodo, $C_{1-4}$ alkoxy and $C_{1-4}$ fluoroalkoxy;

and one or more of the atoms of formula Ia is optionally a detectable isotope;

as a free base or a pharmaceutically acceptable salt, solvate or solvate of a salt thereof, with the following provisos:

when R1 and R2 both are H, and $X_2$ and $X_4$ both are N, R3 is not NH($C_{0-1}$ alkylene)G2, G1, chloro, hydroxy, SCH$_3$, NH$C_{0-1}$ alkyl, N($C_{1-2}$ alkyl)$_2$, NHNH$_2$ or NHOH;

When R1 and R2 both are H, and either of $X_2$ and $X_4$ is N while the other is C, R3 is not chloro, hydroxy or methyl;

when R3 is amino and $X_2$ and $X_4$ both are N, R1 or R2 is not methyl, ethyl, chloro or bromo;

the compound is not 2-(5-aminopyridin-2-yl)-1,3-benzoxazol-6-amine;

5-(6-methyl-1,3-benzoxazol-2-yl)pyrimidin-2-amine;

5-(6-methoxy-1,3-benzoxazol-2-yl)-N-phenylpyrimidin-2-amine;

2-(5-methylpyridin-2-yl)-1,3-benzoxazole; or 5-methyl-2-(6-methylpyridin-3-yl)-1,3-benzoxazole.

In one aspect of the invention, there is provided compounds represented by formula I:

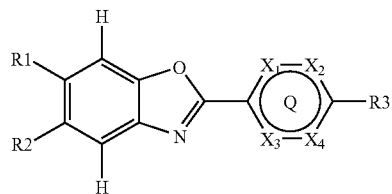
I wherein

R1 is selected from hydrogen, halo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO)$C_{1-3}$ alkyl, NH(CO)$C_{1-3}$ fluorolkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), nitro and cyano;

R2 is selected from hydrogen, fluoro, bromo, iodo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene) and cyano;

R3 is selected from halo, $C_{1-4}$ alkyl, $C_{1-4}$ fluoroalkyl, $C_{1-3}$ alkyleneO$C_{1-3}$ alkyl, $C_{1-3}$ alkyleneO$C_{1-3}$ fluoroalkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-4}$ alkoxy, $C_{1-4}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH($C_{0-3}$ alkylene)G2, N($C_{0-1}$ alkyl)N($C_{0-1}$ alkyl)$_2$, N($C_{0-1}$ alkyl)O$C_{0-1}$ alkyl, N$C_{1-3}$ alkyl(CO)$C_{1-3}$ alkyl, NH(CO)$C_{1-3}$ alkyl, NH(CO)$C_{1-3}$ fluoroalkyl, NH(CO)G2, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), (CO)G2, (CO)NH$_2$G2, S$C_{1-3}$ alkyl, S$C_{1-3}$ fluoroalkyl, SO$_2$NH$_2$, SO$_2$NH$C_{1-3}$ alkyl, SO$_2$NH$C_{1-3}$ fluoroalkyl, SO$_2$N($C_{1-3}$ alkyl)$_2$, SO$_2$N($C_{1-3}$ fluoroalkyl)$_2$, SO$_2$N($C_{1-3}$ alkyl)$C_{1-3}$ fluoroalkyl, cyano and G1, wherein G1 is;

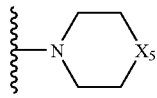

$X_5$ is selected from O, NH, $NC_{1-3}$ alkyl and $NC_{1-3}$ fluoroalkyl;

G2 is phenyl or a 5- or 6-membered aromatic heterocycle and optionally substituted with a substituent from fluoro, bromo, iodo, methyl and methoxy;

Q is a 6-membered aromatic heterocycle containing either one or two N-atoms, wherein $X_1$, $X_2$, $X_3$ and $X_4$ are independently selected from N or C, and wherein one or two of $X_1$, $X_2$, $X_3$ and $X_4$ is N and the remaining is C, and wherein a substituent attached to $X_1$, $X_2$, $X_3$ or $X_4$ is hydrogen when this atom is C;

and one or more of the atoms of formula I is optionally a detectable isotope;

as a free base or a pharmaceutically acceptable salt, solvate or solvate of a salt thereof, with the provisos:

When R1 and R2 both are H, and $X_2$ and $X_4$ both are N, R3 is not $NH(C_{0-1}$ alkylene)G2, G1, chloro, hydroxy, $SCH_3$, $NHC_{0-1}$ alkyl, $N(C_{1-2}$ alkyl$)_2$, $NHNH_2$ or NHOH;

When R1 and R2 both are H, and either of $X_2$ and $X_4$ is N while the other is C, R3 is not chloro, hydroxy or methyl;

When R3 is amino and $X_2$ and $X_4$ both are N, R1 or R2 is not methyl, ethyl or bromo; the compound is not 2-(5-aminopyridin-2-yl)-1,3-benzoxazol-6-amine;

5-(6-methyl-1,3-benzoxazol-2-yl)pyrimidin-2-amine, 5-(6-methoxy-1,3-benzoxazol-2-yl)-N-phenylpyrimidin-2-amine;

2-(5-methylpyridin-2-yl)-1,3-benzoxazole; or 5-methyl-2-(6-methylpyridin-3-yl)-1,3-benzoxazole.

The compounds 2-(5-aminopyridin-2-yl)-1,3-benzoxazol-6-amine, 5-(6-methyl-1,3-benzoxazol-2-yl)pyrimidin-2-amine, 5-(6-methoxy-1,3-benzoxazol-2-yl)-N-phenylpyrimidin-2-amine, 2-(5-methylpyridin-2-yl)-1,3-benzoxazole and 5-methyl-2-(6-methylpyridin-3-yl)-1,3-benzoxazole have the structures as set out below and have previously been described for other purposes as set out in JP 1988/094248; Yoshino et al. J. Med. Chem. 1989, 32, 1528; Yamaguchi et al. Nippon Kagaku Kaishi 1973, 5, 991; Thakak et al. J. Ind. Chem. Soc. 1984, 61, 550; Maruyama et al. Kogyo Kagaku Zasshi 1965, 68, 2423 and Jayanth et al. Ind. J. Chem. 1973, 11, 1112.

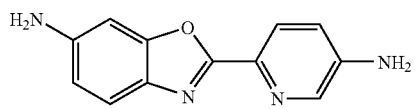

2-(5-aminopyridin-2-yl)-1,3-benzoxazol-6-amine

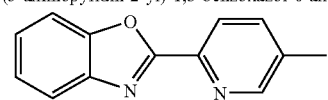

2-(5-methylpyridin-2-yl)-1,3-benzoxazole

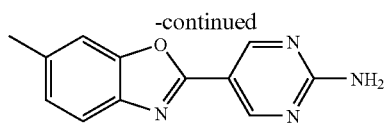

5-(6-methyl-1,3-benzoxazol-2-yl)pyrimidin-2-amine

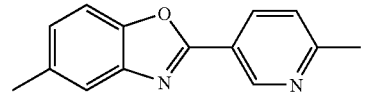

5-methyl-2-(6-methylpyridin-3-yl)-1,3-benzoxazole

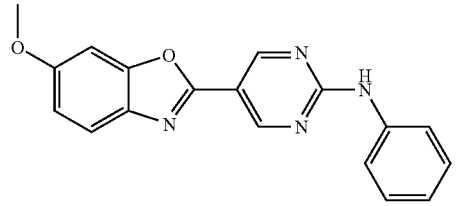

5-(6-methoxy-1,3-benzoxazol-2-yl)-N-phenylpyrimidin-2-amine

In another aspect of the invention, there are provided compounds of formula I or Ia, wherein R1 is selected from hydrogen, halo, $C_{1-6}$ alkyl, $C_{1-6}$ fluoroalkyl, hydroxy, $C_{1-6}$ alkoxy, $C_{1-6}$ fluoroalkoxy, amino, $NHC_{1-3}$ alkyl, $NHC_{1-3}$ fluoroalkyl, $N(C_{1-3}$ alkyl$)_2$, $NH(CO)C_{1-3}$ alkyl, $NH(CO)C_{1-3}$ fluoroalkyl, $(CO)NH_2$, $(CO)NHC_{1-3}$ alkyl, $(CO)NHC_{1-3}$ fluoroalkyl and $(CO)C_{1-3}$ alkoxy.

In another aspect of the invention, there are provided compounds of formula I or Ia, wherein R1 is selected from fluoro, bromo, iodo, methyl, $C_{1-6}$ fluoroalkyl, hydroxy, $C_{1-6}$ alkoxy, $C_{1-6}$ fluoroalkoxy, $NHC_{1-3}$ alkyl, $NHC_{1-3}$ fluoroalkyl, $(CO)NH_2$, $(CO)NHC_{1-3}$ fluoroalkyl and $(CO)C_{1-3}$ alkoxy.

In another aspect of the invention, there are provided compounds of formula I or Ia, wherein R1 is selected from hydroxy, $(CO)C_{1-3}$ alkoxy and $C_{1-6}$ alkoxy, said $C_{1-6}$ alkoxy being methoxy.

In another aspect of the invention, there are provided compounds of formula I or Ia, wherein R2 is selected from hydrogen, fluoro, bromo, iodo, $C_{1-6}$ alkyl, $C_{1-6}$ fluoroalkyl, hydroxy, $C_{1-6}$ alkoxy, amino, $NHC_{1-3}$ alkyl, $NHC_{1-3}$ fluoroalkyl, $N(C_{1-3}$ alkyl$)_2$, $NH(CO)C_{1-3}$ alkyl, $NH(CO)C_{1-3}$ fluoroalkyl, $(CO)NH_2$, $(CO)NHC_{1-3}$ alkyl and $(CO)NHC_{1-3}$ fluoroalkyl.

In another aspect of the invention, there are provided compounds of formula I or Ia, wherein R2 is selected from hydrogen, fluoro, bromo, iodo, methyl, $C_{1-6}$ fluoroalkyl, hydroxy, $C_{1-6}$ alkoxy, said $C_{1-6}$ alkoxy being methoxy, $NHC_{1-3}$ alkyl and $(CO)NH_2$.

In another aspect of the invention, there are provided compounds of formula I or Ia, wherein R2 is hydrogen.

In another aspect of the invention, there are provided compounds of formula I or Ia, wherein Q is Q1.

In another aspect of the invention, there are provided compounds of formula I or Ia, wherein R3 is selected from fluoro, bromo, iodo, hydroxy, $C_{1-4}$ alkoxy, $C_{1-4}$ fluoroalkoxy, amino, $NHC_{1-3}$ alkyl, $NHC_{1-3}$ fluoroalkyl, $N(C_{1-3}$ alkyl$)_2$, $NC_{1-3}$ alkyl$(CO)C_{1-3}$ alkyl, $N(C_{1-3}$ fluoroalkyl$)_2$, $N(C_{1-3}$ alkyl$)C_{1-3}$ fluoroalkyl, $NH(CO)C_{1-3}$ alkyl, $(CO)NH_2$, $(CO)NHC_{1-3}$ alkyl, $(CO)NHC_{1-3}$ fluoroalkyl and G1, wherein $X_5$ is selected from O, NH, NMe and $NC_{1-3}$fluoroalkyl.

In another aspect of the invention, there are provided compounds of formula I or Ia, wherein R3 is selected from fluoro, bromo, $C_{1-4}$ alkoxy, $C_{1-4}$ fluoroalkoxy, amino, $NHC_{1-3}$ alkyl, NHC$_{1-3}$ fluoroalkyl, N(C$_{1-3}$ alkyl)$_2$, NC$_{1-3}$ alkyl(CO)C$_{1-3}$ alkyl, (CO)NH$_2$, (CO)NHC$_{1-3}$ fluoroalkyl and G1, wherein G1 is;

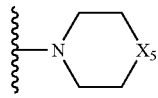

and X$_5$ is O.

In one embodiment of this aspect, R3 is selected from C$_{1-4}$ alkoxy, C$_{1-4}$ fluoroalkoxy, NHC$_{1-3}$ alkyl, N(C$_{1-3}$ alkyl)$_2$, NHC$_{1-3}$ fluoroalkyl and NC$_{1-3}$ alkyl(CO)C$_{1-3}$ alkyl.

In another aspect of the invention, there are provided compounds of formula I or Ia, wherein Q is a pyridine ring, wherein X$_1$ and X$_2$ are independently selected from N or C, and wherein one of X$_1$ and X$_2$ is N and the remaining of X$_1$, X$_2$, X$_3$ and X$_4$ are C.

In one embodiment of this aspect, Q1 is a pyridine ring, wherein X$_2$ is N, and X$_1$, X$_3$ and X$_4$ are C.

In another embodiment of this aspect, Q1 is a pyridine ring, wherein X$_4$ is N, and X$_1$, X$_2$ and X$_3$ are C.

In another embodiment of this aspect, Q1 is a pyridine ring, wherein X$_3$ is N, and X$_1$, X$_2$ and X$_4$ are C.

In another aspect of the invention, there are provided compounds of formula I or Ia, wherein Q is a pyrimidine ring, wherein X$_2$ and X$_4$ are N, and X$_1$ and X$_3$ are C.

In another aspect of the invention, there are provided compounds of formula I or Ia, wherein R5 is selected from fluoro and C$_{1-4}$ alkyl.

In another aspect of the invention, there are provided compounds of formula I or Ia, wherein R1 is hydroxy or C$_{1-6}$ alkoxy, said C$_{1-6}$ alkoxy being methoxy; R2 is hydrogen, R3 is selected from C$_{1-4}$ alkoxy, C$_{1-4}$ fluoroalkoxy, NHC$_{1-3}$ alkyl, N(C$_{1-3}$ alkyl)$_2$, NHC$_{1-3}$ fluoroalkyl and NC$_{1-3}$ alkyl(CO)C$_{1-3}$ alkyl; Q is a pyridine ring, wherein X$_1$ and X$_2$ are independently selected from N or C, and wherein one of X$_1$ and X$_2$ is N and the remaining of X$_1$, X$_2$, X$_3$ and X$_4$ are C.

In another aspect of the invention, there are provided compounds of formula Ia, wherein Q is selected from Q2, Q4 and Q5.

In another aspect of the invention, there are provided compounds of formula Ia, wherein Q is Q5, R1 is C$_{1-6}$ alkoxy, said C$_{1-6}$ alkoxy being methoxy and R2 is hydrogen.

In another aspect of the invention, there are provided compounds of formula Ia, wherein Q is Q4, R1 is C$_{1-6}$ alkoxy, said C$_{1-6}$ alkoxy being methoxy, R2 is hydrogen, R6 is (CO)C$_{1-4}$ alkoxy and R7 is C$_{1-4}$ alkoxy.

In another aspect of the invention, there are provided compounds of formula Ia, wherein Q is Q2, R1 is C$_{1-6}$ alkoxy, said C$_{1-6}$ alkoxy being methoxy and R2 is hydrogen.

In another aspect of the invention, there are provided compounds of formula I or Ia, selected from:

5-(6-Methoxy-1,3-benzoxazol-2-yl)-N,N-dimethylpyridin-2-amine;
2-[6-(Dimethylamino)pyridin-3-yl]-1,3-benzoxazol-6-ol;
5-(6-Methoxy-1,3-benzoxazol-2-yl)-N-methylpyridin-2-amine;
5-(6-Methoxy-1,3-benzoxazol-2-yl)-N,N-dimethylpyridin-2-amine;
N-[5-(6-Methoxy-1,3-benzoxazol-2-yl)pyridin-2-yl]-N-methylacetamide;
2-[6-(Methylamino)pyridin-3-yl]-1,3-benzoxazol-6-ol;
[N-Methyl-$^3$H$_3$]-[5-(6-Methoxy-benzooxazol-2-yl)-pyridin-2-yl]-dimethyl-amine;
[N-Methyl-$^3$H$_3$]-2-(6-Dimethylamino-pyridin-3-yl)-benzooxazol-6-ol;
[O-Methyl-$^3$H$_3$]-[5-(6-Methoxy-benzooxazol-2-yl)-pyridin-2-yl]-methyl-amine;
[N-Methyl-$^3$H$_3$]-[5-(6-Methoxy-benzooxazol-2-yl)-pyridin-2-yl]-methyl-amine;
[N-Methyl-$^3$H$_3$]-2-(6-Methylamino-pyridin-3-yl)-benzooxazol-6-ol;
5-(5-Methoxy-1,3-benzoxazol-2-yl)-N,N-dimethylpyridin-2-amine;
2-[6-(Dimethylamino)pyridin-3-yl]-1,3-benzoxazol-5-ol;
5-(6-Methoxy-1,3-benzoxazol-2-yl)-N,N-dimethylpyrimidin-2-amine;
2-[2-(Dimethylamino)pyrimidin-5-yl]-1,3-benzoxazol-6-ol;
2-(6-Bromopyridin-3-yl)-6-methoxy-1,3-benzoxazole;
2-[6-(2-Fluoroethoxy)pyridin-3-yl]-6-methoxy-1,3-benzoxazole;
2-(5-Bromopyridin-2-yl)-6-methoxy-1,3-benzoxazole;
5-(6-Methoxy-1,3-benzoxazol-2-yl)pyridin-2-amine;
N-(2-Fluoroethyl)-5-(6-methoxy-1,3-benzoxazol-2-yl)pyridin-2-amine;
5-(6-Methoxy-1,3-benzoxazol-2-yl)pyrimidin-2-amine;
N-(2-Fluoroethyl)-5-(6-methoxy-1,3-benzoxazol-2-yl)pyrimidin-2-amine;
[N-Methyl-$^3$H$_3$]-2-(2-Dimethylamino-pyrimidin-5-yl)-benzooxazol-6-ol;
5-(6-Methoxy-1,3-benzoxazol-2-yl)-N-methylpyrimidin-2-amine;
2-(6-Methoxypyridin-3-yl)-1,3-benzoxazol-6-ol;
2-(6-Morpholin-4-ylpyridin-3-yl)-1,3-benzoxazole;
6-Methoxy-2-(6-methoxypyridin-3-yl)benzooxazole;
2-Benzofuran-2-yl-6-methoxy-benzooxazole;
tert-Butyl 5-methoxy-2-(6-methoxybenzooxazol-2-yl)indole-1-carboxylate;
2-(6-Fluoro-5-methyl-pyridin-3-yl)-6-methoxy-benzooxazole;
2-(5-Fluoro-6-methoxy-pyridin-3-yl)-6-methoxy-benzooxazole;
2-(1H-indol-5-yl)-6-methoxy-benzooxazole;
5-(6-Methoxy-1,3-benzoxazol-2-yl)-2-fluoropyridine;
Methyl 2-[2-(dimethylamino)pyrimidin-5-yl]-1,3-benzoxazole-6-carboxylate; and
2-{6-[(2-Fluoroethyl)amino]pyridin-3-yl}-1,3-benzoxazol-6-ol;

as a free base or a pharmaceutically acceptable salt, solvate or solvate of a salt thereof.

In another aspect of the invention, there are provided compounds of formula Ia, wherein, comprising one atom belonging to the group of $^{11}$C, $^{18}$F, $^{123}$I or $^{125}$I, wherein: one of R1 and R2 is either hydroxy, iodo, $^{123}$I, $^{125}$I or [$^{11}$C]methoxy, and the other one of R1 and R2 is H;

R3 is selected from NHMe, NMe2, NH$^{11}$CH$_3$, N(Me)$^{11}$CH$_3$, NHCH$_2$CH$_2$$^{18}$F and OCH$_2$CH$_2$$^{18}$F Q is Q1, wherein X$_2$ and X$_4$ are independently selected from N or C and wherein X$_1$ and X$_3$ are C.

In another aspect of the invention, there are provided compounds of formula I, comprising one atom belonging to the group of $^{11}$C, $^{123}$I or $^{125}$I, wherein:

one of R1 and R2 is either hydroxy, iodo, $^{123}$I, $^{125}$I or [$^{11}$C]methoxy, and the other one of R1 and R2 is H;

R3 is selected from NHMe, NMe2, NH$^{11}$CH$_3$ and N(Me)$^{11}$CH$_3$;

Q is a pyridine ring, wherein X$_3$ and X$_4$ are independently selected from N or C, and wherein one of X$_3$ and X$_4$ is N and the remaining of X$_1$, X$_2$, X$_3$ and X$_4$ are C.

In another aspect of the invention, there are provided compounds of formula I or Ia, wherein one or more of the atoms of R1 is a radiolabeled atom.

In another aspect of the invention, there are provided compounds of formula I or Ia, wherein one or more of the atoms of R2 is a radiolabeled atom.

In another aspect of the invention, there are provided compounds of formula I or Ia, wherein one or more of the atoms of R3 is a radiolabeled atom.

In another aspect of the invention, there are provided compounds of formula I or Ia, wherein said radiolabeled atom is selected from $^{3}$H, $^{18}$F, $^{19}$F, $^{11}$C, $^{13}$C, $^{14}$C, $^{75}$Br, $^{76}$Br, $^{120}$I, $^{123}$I, $^{125}$I and $^{131}$I.

In one embodiment of this aspect, said radiolabeled atom is selected from $^{3}$H, $^{18}$F, $^{19}$F, $^{11}$C, $^{14}$C and $^{123}$I.

In another embodiment of this aspect, said radiolabeled atom is selected from $^{123}$I, $^{18}$F and $^{11}$C.

In another embodiment of this aspect, said radiolabeled atom is $^{11}$C.

In another embodiment of this aspect, said radiolabeled atom is $^{18}$F.

In another embodiment of this aspect, said radiolabeled atom is $^{123}$I.

In another aspect of the invention, there are provided compounds of formula Ib:

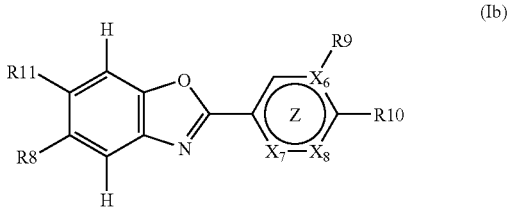

(Ib)

Z is a 6-membered aromatic heterocycle containing one or two N atoms, wherein $X_6$, $X_7$ and $X_8$ are independently selected from N or C, and wherein one or two of $X_6$, $X_7$ and $X_8$ is N and the remaining is C, and wherein $X_6$ is C, said C being optionally substituted with R9;

R8 is selected from OSi(G3)$_3$, OCH$_2$G4, OG5, H, bromo, fluoro, hydroxy, methoxy, Sn(C$_{1-4}$ alkyl)$_3$, N(CH$_3$)$_3^+$, IG6$^+$, N$_2^+$ and nitro;

R9 is selected from H, bromo, fluoro, Sn(C$_{1-4}$ alkyl)$_3$, N(CH$_3$)$_3^+$, IG6$^+$, N$_2^+$ and nitro;

R10 is selected from amino, methylamino, NH(CH$_2$)$_{2-4}$G7, dimethylamino, methoxy, hydroxy, (CO)NH$_2$, (CO)NH(CH$_2$)$_{2-4}$G7 and O(CH$_2$)$_{2-4}$G7;

R11 is selected from OSi(G3)$_3$, OCH$_2$G4, OG5, (CO)NH$_2$, (CO)NH(CH$_2$)$_{2-4}$G7, H, bromo, fluoro, hydroxy, methoxy, Sn(C$_{1-4}$ alkyl)$_3$, N(CH$_3$)$_3^+$, IG6$^+$, N$_2^+$ and nitro;

G3 is selected from C$_{1-4}$ alkyl and phenyl;

G4 is selected from 2-(trimethylsilyl)ethoxy, C$_{1-3}$ alkoxy, 2-(C$_{1-3}$ alkoxy)ethoxy, C$_{1-3}$ alkylthio, cyclopropyl, vinyl, phenyl, p-methoxyphenyl, o-nitrophenyl, and 9-anthryl;

G5 is selected from tetrahydropyranyl, 1-ethoxyethyl, phenacyl, 4-bromophenacyl, cyclohexyl, t-butyl, t-butoxycarbonyl, 2,2,2-trichloroethylcarbonyl and triphenylmethyl;

IG6$^+$ is a constituent of a iodonium salt, in which the iodo atom is hyper-valent and has a positive formal charge and, in which, G6 is phenyl, optionally substituted with one substituent selected from methyl and bromo;

G7 is selected from bromo, iodo, OSO$_2$CF$_3$, OSO$_2$CH$_3$ and OSO$_2$phenyl, said phenyl being optionally substituted with methyl or bromo;

with reference to formula Ib, one or several of the substituents selected from R8, R9, R10 and R11 is one of the functional groups selected from bromo, fluoro, hydroxy, Sn(C$_{1-4}$ alkyl)$_3$, N(CH$_3$)$_3^+$, IG6$^+$, N$_2^+$, nitro, amino, methylamino, NH(CH$_2$)$_{2-4}$G7, (CO)NH(CH$_2$)$_{2-4}$G7 and O(CH$_2$)$_{2-4}$G7;

as a free base or a salt, solvate or solvate of a salt thereof,

In another aspect of the invention, there are provided compounds of formula Ib, wherein R8 is H; R9 is H; R10 is selected from amino, methylamino, dimethylamino, NH(CH$_2$)$_{2-4}$G7, methoxy, hydroxy, (CO)NH$_2$, (CO)NH(CH$_2$)$_{2-4}$G7 and O(CH$_2$)$_{2-4}$G7; R11 is selected from OSi(CH$_3$)$_2$C(CH$_3$)$_3$, (CO)NH$_2$, (CO)NH(CH$_2$)$_{2-4}$G7, H, fluoro, hydroxy, methoxy, Sn(C$_{1-4}$ alkyl)$_3$ and N$_2^+$.

In another aspect of the invention, there are provided compounds of formula Ib, wherein and $X_6$ and $X_7$ are C, and $X_8$ is N.

In another aspect of the invention, there are provided compounds of formula Ib, wherein Z is a pyridine ring, wherein $X_6$ and $X_8$ are C, and wherein $X_7$ is N.

In another aspect of the invention, there are provided compounds of formula Ib, wherein $X_6$ and $X_8$ are N, and wherein $X_7$ is C.

In another aspect of the invention, there are provided compounds of formula Ib, selected from:

2-[6-(Dimethylamino)pyridin-3-yl]-1,3-benzoxazol-6-ol;
5-(6-Methoxy-1,3-benzoxazol-2-yl)-N-methylpyridin-2-amine;
2-[6-(Methylamino)pyridin-3-yl]-1,3-benzoxazol-6-ol;
2-[6-(Dimethylamino)pyridin-3-yl]-1,3-benzoxazol-5-ol;
2-[2-(Dimethylamino)pyrimidin-5-yl]-1,3-benzoxazol-6-ol;
2-(6-Bromopyridin-3-yl)-6-methoxy-1,3-benzoxazole;
2-(5-Bromopyridin-2-yl)-6-methoxy-1,3-benzoxazole;
5-(6-Methoxy-1,3-benzoxazol-2-yl)pyridin-2-amine;
5-(6-Methoxy-1,3-benzoxazol-2-yl)pyrimidin-2-amine;
5-(6-Methoxy-1,3-benzoxazol-2-yl)-N-methylpyrimidin-2-amine;
2-(6-Methoxypyridin-3-yl)-1,3-benzoxazol-6-ol;
2-(6-Fluoro-5-methyl-pyridin-3-yl)-6-methoxy-benzooxazole;
2-(1H-Indol-5-yl)-6-methoxy-benzooxazole;
5-(6-Methoxy-1,3-benzoxazol-2-yl)-2-fluoropyridine;
2-(6-Aminopyridin-3-yl)-1,3-benzoxazol-6-ol;
5-(6-{[tert-Butyl(dimethyl)silyl]oxy}-1,3-benzoxazol-2-yl)pyridin-2-amine;
tert-Butyl [5-(6-methoxy-1,3-benzoxazol-2-yl)pyrimidin-2-yl]carbamate; and
tert-Butyl [5-(6-methoxy-1,3-benzoxazol-2-yl)pyridin-2-yl]carbamate.

In another aspect of the invention, there is provided use of a compound of formula Ib, as synthetic precursor in a process for preparation of a labeled compound, wherein the said label is constituted by one [$^{11}$C]methyl group.

In another aspect of the invention, there is provided use of a compound of formula Ib, as synthetic precursor in a process for preparation of a labeled compound, wherein the said label is constituted by one $^{18}$F atom.

In another aspect of the invention, there is provided use of a compound of formula Ib, as synthetic precursor in a process for preparation of a labeled compound, wherein the said label is constituted by one atom selected from $^{120}$I, $^{123}$I, $^{125}$I and $^{131}$I.

In another aspect of the invention, there is provided a pharmaceutical composition comprising a compound of formula I or Ia, together with a pharmaceutically acceptable carrier.

In another aspect of the invention, there is provided a pharmaceutical composition for in vivo imaging of amyloid deposits, comprising a compound of formula I or Ia, together with a pharmaceutically acceptable carrier.

In another aspect of the invention, there is provided an in vivo method for measuring amyloid deposits in a subject; comprising the steps of: (a) administering a detectable quantity of a pharmaceutical composition comprising a compound of formula I or Ia, together with a pharmaceutically acceptable carrier, and detecting the binding of the compound to amyloid deposit in the subject.

In one embodiment of this aspect, said detection is carried out by gamma imaging, magnetic resonance imaging and magnetic resonance spectroscopy.

In another aspect of the invention, said in vivo method for measuring amyloid deposits in a subject, the subject is suspected of having a disease or syndrome selected from the group consisting of Alzheimer's Disease, familial Alzheimer's Disease, Down's Syndrome and homozygotes for the apolipoprotein E4 allele.

In another aspect of the invention, there is provided compounds of formula I or Ia, for use in therapy.

In another aspect of the invention, there is provided use of compounds of formula I or Ia, in the manufacture of a medicament for prevention and/or treatment of Alzheimer's Disease, familial Alzheimer's Disease, Down's Syndrome and homozygotes for the apolipoprotein E4 allele.

DEFINITIONS

As used herein, "alkyl", "alkylenyl" or "alkylene" used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{1-6}$ alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N($C_0$ alkyl)$_2$" is equivalent to "$NH_2$" (amino). When the specific number denoting the alkylenyl or alkylene-group is the integer 0 (zero), a bond is intended to link the groups onto which the alkylenyl or alkylene-group is substituted. For example, "NH($C_0$ alkylene)$NH_2$" is equivalent to "$NHNH_2$" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "N($C_4$ alkylene)", "N($C_5$ alkylene)" and "N($C_2$ alkylene)$_2NH$" is equivalent to pyrrolidinyl, piperidinyl and piperazinyl, respectively.

Examples of alkyl include, but are not limited to, methyl, ethyl, n-propyl, i-propyl, n-butyl, i-butyl, sec-butyl, t-butyl, pentyl, and hexyl.

Examples of alkylene or alkylenyl include, but are not limited to, methylene, ethylene, propylene, and butylene.

As used herein, "alkoxy" or "alkyloxy" represents an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to the carbon(s) of the corresponding alkyl, alkylene and alkoxy-groups are replaced by fluoro. Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "aromatic" refers to hydrocarbonyl groups having one or more unsaturated carbon ring(s) having aromatic characters, (e.g. 4n+2 delocalized electrons) and comprising up to about 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 or 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "cycloalkyl" is intended to include saturated ring groups, having the specified number of carbon atoms. These may include fused or bridged polycyclic systems. Preferred cycloalkyls have from 3 to 10 carbon atoms in their ring structure, and more preferably have 3, 4, 5, or 6 carbons in the ring structure. For example, "$C_{3-6}$ cycloalkyl" denotes such groups as cyclopropyl, cyclobutyl, cyclopentyl, or cyclohexyl.

As used herein, "halo" or "halogen" refers to fluoro, chloro, bromo, and iodo. "Counterion" is used to represent a small, negatively charged species such as chloride, bromide, hydroxide, acetate, sulfate, tosylate, benezensulfonate, and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally replaced by a —C(O)—; and where unless stated to the contrary a ring nitrogen or sulphur atom is optionally oxidised to form the N-oxide or S-oxide(s) or a ring nitrogen is optionally quarternized; wherein a ring —NH is optionally substituted by acetyl, formyl, methyl or mesyl; and a ring is optionally substituted by one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms. In some embodiments, the heteroaryl group has 1 heteroatom.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used.

As used herein, "in vivo hydrolysable precursors" means an in vivo hydrolysable (or cleavable) ester of a compound of formula I that contains a carboxy or a hydroxy group. For example amino acid esters, $C_{1-6}$ alkoxymethyl esters like methoxymethyl; $C_{1-6}$ alkanoyloxymethyl esters like pivaloyloxymethyl; $C_{3-8}$ cycloalkoxycarbonyloxy $C_{1-6}$ alkyl esters like 1-cyclohexylcarbonyloxyethyl, acetoxymethoxy, or phosphoramidic cyclic esters.

As used herein, "tautomer" means other structural isomers that exist in equilibrium resulting from the migration of a hydrogen atom. For example, keto-enol tautomerism where the resulting compound has the properties of both a ketone and an unsaturated alcohol.

As used herein "stable compound" and "stable structure" are meant to indicate a compound that is sufficiently robust to survive isolation to a useful degree of purity from a reaction mixture, and formulation into an efficacious therapeutic or diagnostic agent.

Compounds of the invention further include hydrates and solvates.

The present invention includes isotopically labeled compounds of the invention. An "isotopically-labeled", "radiolabeled", "labeled", "detectable" or "detectable amyloid binding" compound, or a "radioligand" is a compound of the invention where one or more atoms are replaced or substituted by an atom having an atomic mass or mass number different from the atomic mass or mass number typically found in nature (i.e., naturally occurring). Suitable radionuclides (i.e. "detectable isotopes") that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radiolabeled compounds will depend on the specific application of that radiolabeled compound. For example, for in vitro plaque or receptor labeling and competition assays, compounds that incorporate $^{3}H$, $^{14}C$, or $^{125}I$ will generally be most useful. For in vivo imaging applications $^{11}C$, $^{13}C$, $^{18}F$, $^{19}F$, $^{120}I$, $^{123}I$, $^{131}I$, $^{75}Br$, or $^{76}Br$ will generally be most useful.

Examples of an "effective amount" include amounts that enable imaging of amyloid deposit(s) in vivo, that yield acceptable toxicity and bioavailability levels for pharmaceutical use, and/or prevent cell degeneration and toxicity associated with fibril formation.

This invention also provides radiolabeled heteroaryl substituted benzoxazoles as amyloid imaging agents.

Methods of Use

The compounds of the present invention may be used to determine the presence, location and/or amount of one or more amyloid deposit(s) in an organ or body area, including the brain, of an animal. Amyloid deposit(s) include, without limitation, deposit(s) of Aβ. In allowing the temporal sequence of amyloid deposition to be followed, the inventive compounds may farther be used to correlate amyloid deposition with the onset of clinical symptoms associated with a disease, disorder or condition. The inventive compounds may ultimately be used to, and to diagnose a disease, disorder or condition characterized by amyloid deposition, such as AD, familial AD, Down's syndrome, amyloidosis and homozygotes for the apolipoprotein E4 allele.

The method of this invention determines the presence and location of amyloid deposits in an organ or body area, preferably brain, of a patient. The present method comprises administration of a detectable quantity of a pharmaceutical composition containing an amyloid-binding compound of the present invention called a "detectable compound," or a pharmaceutically acceptable water-soluble salt thereof, to a patient. A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid probes which, in conjunction with non-invasive neuroimaging techniques such as magnetic resonance spectroscopy (MRS) or imaging (MINI), or gamma imaging such as positron emission tomography (PET) or single-photon emission computed tomography (SPECT), are used to quantify amyloid deposition in vivo. The term "in vivo imaging" refers to any method which permits the detection of a labeled heteroaryl substituted benzoxazole derivative as described herein. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having dementia.

For purposes of in vivo imaging, the type of detection instrument available is a major factor in selecting a given label. For instance, radioactive isotopes and $^{19}F$ are particularly suitable for in vivo imaging in the methods of the present invention. The type of instrument used will guide the selection of the radionuclide or stable isotope. For instance, the radionuclide chosen must have a type of decay detectable by a given type of instrument.

Another consideration relates to the half-life of the radionuclide. The half-life should be long enough so that it is still detectable at the time of maximum uptake by the target, but short enough so that the host does not sustain deleterious radiation. The radiolabeled is compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range.

For PET detection, the radiolabel will be a positron-emitting radionuclide, such as $^{18}F$ or $^{11}C$, which will annihilate to form two gamma rays which will be detected by the PET camera.

In the present invention, amyloid binding compounds/probes are made which are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the heteroaryl substituted benzoxazole derivatives may be labeled with $^{19}F$ or $^{13}C$ for MRS/MRI by general organic chemistry techniques known to the art. The compounds may also be radiolabeled with $^{18}F$, $^{11}C$, $^{75}Br$, $^{76}Br$, or $^{120}I$ for PET by techniques well known in the art and are described by Fowler, J. and Wolf, A. in POSITRON EMISSION TOMOGRAPHY AND AUTORADIOGRAPHY 391-450 (Raven Press, 1986). The compounds also may be radiolabeled with $^{123}I$ and $^{131}I$ for SPECT by any of several techniques known to the art. See, e.g., Kulkarni, Int. J. Rad. Appl. & Inst. (Part B) 18: 647 (1991). The compounds may also be radiolabeled with known metal radiolabels, such as Technetium-99m ($^{99m}Tc$). Modification of the substituents to introduce ligands that bind such metal ions can be effected without undue experimentation by one of ordinary skill in the radiolabeling art. The metal radiolabeled compound can then be used to detect amyloid deposits. Preparing radiolabeled derivatives of Tc-99m is well known in the art. See, for example, Zhuang et al. Nuclear Medicine & Biology 26(2):217-24, (1999); Oya et al. Nuclear Medicine & Biology 25(2):135-40, (1998), and Hom et al. Nuclear Medicine & Biology 24(6):485-98, (1997). In addition, the compounds may be labeled with $^{3}H$, $^{14}C$ and $^{125}I$, by methods well known to the one skilled in the art, for detection of amyloid plaque in in vitro and post mortem samples.

The methods of the present invention may use isotopes detectable by nuclear magnetic resonance spectroscopy for purposes of in vivo imaging and spectroscopy. Elements particularly useful in magnetic resonance spectroscopy include $^{19}F$ and $^{13}C$.

Suitable radioisotopes for purposes of this invention include beta-emitters, gamma-emitters, positron-emitters, and x-ray emitters. These radioisotopes include $^{120}I$, $^{123}I$, $^{131}I$, $^{125}I$, $^{18}F$, $^{11}C$, $^{75}Br$, and $^{76}Br$. Suitable stable isotopes for use in Magnetic Resonance Imaging (MRI) or Spectroscopy (MRS), according to this invention, include $^{19}F$ and $^{13}C$. Suitable radioisotopes for in vitro quantification of amyloid in homogenates of biopsy or post-mortem tissue include $^{125}I$, $^{14}C$, and $^{3}H$. The preferred radiolabels are $^{11}C$ and $^{18}F$ for use in PET in vivo imaging, $^{123}I$ for use in SPECT imaging, $^{19}F$ for MRS/MRI, and $^{3}H$ and $^{14}C$ for in vitro studies. However, any conventional method for visualizing diagnostic probes can be utilized in accordance with this invention.

The compounds of the present invention may be administered by any means known to one of ordinary skill in the art. For example, administration to the animal may be local or systemic and accomplished orally, parenterally, by inhalation spray, topically, rectally, nasally, buccally, vaginally, or via an implanted reservoir. The term "parenteral" as used herein includes subcutaneous, intravenous, intraarterial, intramuscular, intraperitoneal, intrathecal, intraventricular, intrasternal, intracranial, and intraosseous injection and infusion techniques.

The exact administration protocol will vary depending upon various factors including the age, body weight, general health, sex and diet of the patient; the determination of specific administration procedures would be routine to any one of ordinary skill in the art.

Dose levels on the order of about 0.001 ug/kg/day to about 10,000 mg/kg/day of an inventive compound are useful for the inventive methods. In one embodiment, the dose level is about 0.001 ug/kg/day to about 10 g/kg/day. In another embodiment, the dose level is about 0.01 ug/kg/day to about 1.0 g/kg/day. In yet another embodiment, the dose level is about 0.1 mg/kg/day to about 100 mg/kg/day.

The specific dose level for any particular patient will vary depending upon various factors, including the activity and the possible toxicity of the specific compound employed; the age, body weight, general health, sex and diet of the patient; the time of administration; the rate of excretion; the drug combination; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods.

The regimen may include pretreatment and/or co-administration with additional therapeutic agent(s).

In one embodiment, the inventive compounds are administered to an animal that is suspected of having or that is at risk of developing a disease, disorder or condition characterized by amyloid deposition. For example, the animal may be an elderly human.

Method for Detecting Amyloid Deposits In Vitro

This invention further provides a method for detecting amyloid deposit(s) in vitro comprising: (i) contacting a bodily tissue with an effective amount of an inventive compound, wherein the compound would bind any amyloid deposit(s) in the tissue; and (ii) detecting binding of the compound to amyloid deposit(s) in the tissue.

The binding may be detected by any means known in the art. Examples of detection means include, without limitation, microscopic techniques, such as bright-field, fluorescence, laser-confocal and cross-polarization microscopy.

Pharmaceutical Compositions

This invention further provides a pharmaceutical composition comprising: (i) an effective amount of at least one inventive compound; and (ii) a pharmaceutically acceptable carrier.

The composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and therapeutic agent(s).

The composition may be formulated into solid, liquid, gel or suspension form for: (1) oral administration as, for example, a drench (aqueous or non-aqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by subcutaneous, intramuscular, intravenous or epidural injection as, for example, a sterile solution, suspension or sustained-release formulation; (3) topical application as, for example, a cream, ointment, controlled-release patch or spray applied to the skin; (4) intravaginal or intrarectal administration as, for example, a pessary, cream or foam; (5) sublingual administration; (6) ocular administration; (7) transdermal administration; or (8) nasal administration.

In one embodiment, the composition is formulated for intravenous administration and the carrier includes a fluid and/or a nutrient replenisher. In another embodiment, the composition is capable of binding specifically to amyloid in vivo, is capable of crossing the blood-brain barrier, is non-toxic at appropriate dose levels and/or has a satisfactory duration of effect. In yet another embodiment, the composition comprises about 10 mg of human serum albumin and from about 0.5 to 500 mg of a compound of the present invention per mL of phosphate buffer containing NaCl.

The present invention further provides compositions comprising a compound of formula I, and at least one pharmaceutically acceptable carrier, diluent or excipient.

The present invention further provides methods of treating or preventing an Aβ-related pathology in a patient, comprising administering to the patient a therapeutically effective amount of a compound of formula I.

The present invention further provides a compound described herein for use as a medicament.

The present invention further provides a compound described herein for the manufacture of a medicament.

Some compounds of formula I may have stereogenic centres and/or geometric isomeric centres (E- and Z-isomers), and it is to be understood that the invention encompasses all such optical isomers, enantiomers, diastereoisomers, atropisomers and geometric isomers.

The present invention relates to the use of compounds of formula I as herein before defined as well as to the salts thereof. Salts for use in pharmaceutical compositions will be pharmaceutically acceptable salts, but other salts may be useful in the production of the compounds of formula I.

Compounds of the invention can be used as medicaments. In some embodiments, the present invention provides compounds of formula I, or pharmaceutically acceptable salts, tautomers or in vivo-hydrolysable precursors thereof, for use as medicaments. In some embodiments, the present invention provides compounds described here in for use as medicaments for treating or preventing an Aβ-related pathology. In some further embodiments, the Aβ-related pathology is Downs syndrome, a β-amyloid angiopathy, cerebral amyloid angiopathy, hereditary cerebral hemorrhage, a disorder associated with cognitive impairment, MCI ("mild cognitive impairment"), Alzheimer Disease, memory loss, attention deficit symptoms associated with Alzheimer disease, neurodegeneration associated with Alzheimer disease, dementia of mixed vascular origin, dementia of degenerative origin, presenile dementia, senile dementia, dementia associated with Parkinson's disease, progressive supranuclear palsy or cortical basal degeneration.

Methods of Preparation

The present invention also relates to processes for preparing the compound of formula I as a free base, acid, or pharmaceutically acceptable salts thereof. Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March 4th ed. McGraw Hill (1992) or, "Organic Synthesis", Smith, McGraw Hill, (1994). Techniques for purification of intermediates and final products include for example, straight and reverse phase chromatography on column or rotating plate, recrystallisation, distillation and liquid-liquid or solid-liquid extraction, which will be readily understood by the one skilled in the art. The definitions of substituents and groups are as in formula I except where defined differently. The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures. The terms "flash chromatography" or "flash column chromatography" shall mean preparative chromatography on silica using an organic solvent, or mixtures thereof, as mobile phase.

| Abbreviations | |
|---|---|
| Ac | acetate; |
| atm | atmosphere; |
| aq. | aqueous; |
| BINAP | 2,2'-bis(diphenylphosphino)-1,1'-binaphtyl |
| dba | dibenzylideneacetone; |
| DCM | dichloromethane; |
| DDQ | 2,3-dichloro-5,6-dicyano-1,4-benzoquinone; |
| DMA | N,N-dimethylacetamide; |
| DME | 1,2-dimethoxyethane; |
| DMF | N,N-dimethylformamide; |
| DMSO | dimethyl sulfoxide; |
| dppf | 1,1'-bis(diphenylphosphino)ferrocene; |
| EtOAc | ethyl acetate; |
| EtOH | ethanol; |
| h | hour; |
| hep | heptane; |
| hex | hexane(s); |
| LAH | lithium aluminumhydride; |
| MeCN | acetonitrile; |
| MeOH | methanol; |
| NHMDS | sodium bis(trimethylsilyl)amide; |
| NMP | 1-methyl-2-pyrrolidinone; |
| o.n. | over night; |
| Pd(dppf)Cl$_2$ | 1,1'-bis(diphenylphosphino)ferrocene dichloropalladium(II); |
| prep. HPLC | preparative HPLC; |
| PTSA | p-toluenesulfonic acid; |
| r.t. | room temperature; |
| r.m. | reaction mixture; |
| sat. | saturated; |
| TFA | trifluoroacetic acid; |
| THF | tetrahydrofurane; |

Preparation of Intermediates

Compounds of formula II, III, IV V and VI are useful intermediates in the preparation of compound of formula Ia and Ib. R1 to R11, and $X_1$ to $X_8$ are defined as in formula Ia and Ib. Compounds of formula II-VI are either commercially available, or can be prepared from either commercially available, or in the literature described compounds. For example, compounds in which one or more of $Y_1, Y_2, Y_3, Y_4$, R1, R2 or R3 does not correspond to the definitions of formula II-VI, can be used for the preparation of compounds of formula II-VI by transformations or introduction of substituents or groups. Such examples are given below:

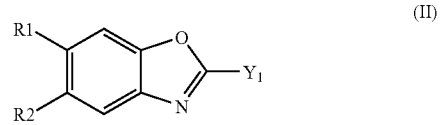

$Y_1$ = H, F, Cl, Br, I, SMe, SCH$_2$(C=O)NH$_2$, Sn(n-Bu)$_3$, ZnX

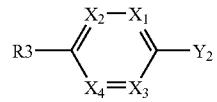

$Y_2$ = F, Cl, Br, I, OTf, SMe, B(OH)$_2$, B(Oalkyl)$_2$, Sn(n-Bu)$_3$, ZnX, CONH$_2$

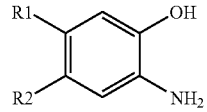

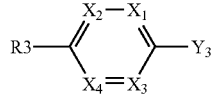

$Y_3$ = CHO, COOH, COCl, CN, COOalkyl, CONH2
or equivalent carboxylic acid derivatives

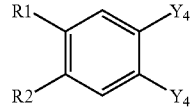

$Y_4$ = Cl, Br, I

1) Preparation of Compounds of Formula III in which $Y_2$ is B(Oalkyl)$_2$, B(OH)$_2$ or ZnX:

a) From the corresponding chlorides, bromides, iodides or triflates through palladium catalysed borylation employing for example bis(pinacolato)diboran or dialkoxyboranes as reagents under palladium catalysis, using for example PdCl$_2$(dppf), or Pd(dba)$_2$ with added tricyclohexylphosphine, as catalysts, together with stochiometric amounts of a base such as KOAc and NEt$_3$ in solvents such as DMSO, DMF, DMA or dioxan at a temperature from r.t. to 80° C., alternatively subsequently followed by acidic hydrolysis (Ishiyama et al. Tetrahedron 2001, 57, 9813; Murata et al. J. Org. Chem. 2000, 65, 164).

b) From the corresponding chlorides, bromides or iodides by initial conversion into an arylmagnesium or lithium reagent by treatment with for example n-BuLi, n-Bu$_3$MgLi or Mg, followed by trapping with a trialkyl borate, preferrably triisopropyl borate, and alternatively subsequent acidic hydrolysis to give the corresponding boronic acid, or with zinc dust to give the corresponding organic Zn-compounds.

2) Preparation of Compounds of Formula III in Which $Y_2$ is a Triflate:

From the corresponding alcohol by conversion into the triflate using O(SO$_2$CF$_3$)$_2$ and a base such as triethylamine or pyridine.

3) Preparation of Compounds of Formula II or III in Which $Y_1$ and $Y_2$, Respectively, is a Thioether, such as Thiomethyl or SCH$_2$(C=O)NH$_2$:

From the corresponding thiol by treatment with methyl iodide or ClCH$_2$(C=O)NH$_2$ in a solvent such as acetone or THF under basic conditions (Richardsson et al. J. Org. Chem. 2005, 70, 7436; Liebeskind et al. Org. Lett. 2002. 4, 979).

4) Preparation of Compounds of Formula II or III in Which $Y_1$ and $Y_2$, Respectively, is $Sn(n-Bu)_3$, $Sn(Me)_3$, $Sn(Ph)_3$ or ZnX:

From the corresponding unsubstitutes benzoxazole ($Y_1$=H) or heteroaromatic halide (e.g. $Y_2$=Br) via metallation with a lithium reagent, such as MeLi or n-BuLi, followed by transmetallation using organotin chlorides such as $Me_3SnCl$ or $n-Bu_3SnCl$, or a zinc salt (Molloy et al. J. Organometallic Chem. 1989, 365, 61; Richardsson et al. J. Org. Chem. 2005, 70, 7436).

5) Preparation of Compounds of Formula II in Which $Y_1$ is Chloro, Bromo or Hydrogen:

a) From intermediates IV, as described in Lok et al. J. Org. Chem. 1996, 61, 3289 and Haviv et al. J. Med. Chem. 1988, 31, 1719, by condensation with potassium O-ethylxantate, by heating in a solvent such as ethanol or pyridine to generate the intermediate thiol (II, $Y_1$=SH), followed by treatment with $PCl_5$, or alternatively $PBr_5$, to generate chloro or bromo compounds II ($Y_1$=Cl or Br), respectively.

b) From intermediates IV by treatment with cyanogen bromide in methanol, or preferably with di(imidazole-1-yl) methanimine in refluxing THF as described in Wu et al. J. Heterocyclic Chem. 2003, 40, 191, to generate amine compounds (II, $Y_1$=$NH_2$), followed by treatment of these with t-butyl nitrite and $CuCl_2$ or $CuBr_2$ (Hodgetts et al. Org. Lett. 2002, 4, 2905), in acetonitrile at 80° C., to generate chloro or bromo compounds (II, $Y_1$=Cl or Br), respectively.

c) From amine compounds (II, $Y_1$=$NH_2$) by deamination employing for example isoamylnitrite in dioxane or THF at elevated temperature (50-85° C.) as described in Nagarajan et al. BioOrg. Med. Chem. Lett. 2003, 4769, to yield hydrogen compounds (II, $Y_1$=H).

Methods of Preparation of Non-Labelled Compounds of Formula Ia and Ib

It is to be understood that a transformation of a group or substituent R1, R2, R3 into another group or substituent by chemical manipulation can be conducted on any final product or on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Non-limiting examples of methods for the preparation of compounds of formula Ia and Ib are given below:

1) Preparation by Palladium or Rhodium-Catalyzed Cross-Coupling Reactions of Intermediates II and III:

a) Palladium catalyzed and copper(I) mediated cross coupling of thioethers of intermediates of formula II (e.g. $Y_1$=SMe, $SCH_2(C$=$O)NH_2$) with boronic acids or esters or stannanes of formula III (e.g. $Y_2$=$B(OH)_2$, $B(Oalkyl)_2$, $Sn(n-Bu)_3$). A palladium catalyst such as $Pd(PPh_3)_4$ or $Pd_2dba_3$ in a solvent, such as THF can be used. (Richardsson et al. J. Org. Chem. 2005, 70, 7436; Liebeskind et al. Org. Lett. 2002, 4, 979).

b) Palladium catalyzed Stille coupling of aryl halides, or pseudo-halides, of intermediate of formula III (e.g. $Y_2$=chloride, bromide, iodide or triflate) with benzoxazole stannanes of formula II (e.g. $Y_1$=$Sn(n-Bu)_3$). A palladium catalyst such as $PdCl_2(PPh_3)_2$ may be used in a solvent, such as xylene, at a temperature from r.t. to 120° C. (Kosugi et al. Bull. Chem. Soc. Jpn. 1986, 59, 677).

c) Palladium catalyzed coupling of aryl halides, or pseudo-halides, of intermediates of formula III (e.g. $Y_2$=chloride, bromide, iodide or triflate) with zincates of formula II (e.g. $Y_1$=ZnX). (Anderson et al. Synthesis 1996, 583)

d) Palladium catalyzed direct arylation of intermediates of formula II ($Y_1$=H) with aryl halides, or pseudo-halides, of intermediate of formula III (e.g. $Y_2$=chloride, bromide, iodide or triflates). A palladium catalyst such as $Pd(OAc)_2$—P(t-Bu)$_3$ may be used in a solvent, such as DMF. (Alagille et al. Tetrahedron Lett. 2005, 46, 1349).

e) Rhodium catalyzed direct arylation of intermediates of formula II ($Y_1$=H) with aryl halides, of intermediate of formula III (e.g. $Y_2$=bromide or iodide). A rhodium catalyst such as $[RhCl(coe)_2]_2/PCy_3$ may be used in a solvent, such as THF under basic conditions at elevated temperatures. (Lewis et al. Org. Lett. 2004, 6, 35).

2) Preparation by Employment of Compounds IV and V as Starting Materials:

a) Condensation of 2-aminophenoles IV with intermediate V in which $Y_3$ is a carboxylic acid, acid chloride, ester, amide, nitrile or their synthetic equivalent by the aid of a catalyst, such as polyphosphoric acid or its ester, boric acid, trimethylsilyl polyphosphate and $SnCl_2$, neat or in solvents such as NMP, xylene and dioxan at a temperature from r.t. to 220° C. by conventional heating or with microwave irradiation. (Gong et al. Bioorg. Med. Chem. Lett. 2004, 14, 1455; Hein et al. J. Am. Chem. Soc. 1957, 79, 427; Terashima et al. Synthesis 1982, 484; Haugwitz et al. J. Med. Chem. 1982, 25, 969; Karlsson et al. Bioorg. & Med. Chem. 2004, 12, 2369; Cho et al J. Heterocyclic Chem. 2002, 39, 421).

b) N-acylation of 2-aminophenoles IV with intermediate V in which $Y_3$ is a carboxylic acid chloride to form an amide bond, followed by thermal and/or acid-catalyzed cyclocondensation to form the benzoxazole ring. Acids such as pyridinium p-toluenesulfonate, PTSA or HOAc can be used. (Wang et al. Bioorg. & Med. Chem. 2004, 12, 17; Haugwitz et al. J. Med. Chem. 1982, 25, 969; DeLuca et al. Tetrahedron Lett 1997, 38, 199).

c) Oxidative cyclization of a phenolic Schiff base, derived from the condensation of 2-aminophenol IV with intermediate V in which $Y_3$ is CHO, using various oxidants such as DDQ, $Pb(OAc)_4$, $ThClO_4$ or $Mn(OAc)_3$. (Chang et al. Tetrahedron Lett. 2002, 43, 951; Park et al. J. Heterocyclic Chem. 2002, 39, 1279; Haugwitz et al. J. Med. Chem. 1982, 25, 969).

3. The Following Route May be Used for the Synthesis of Compounds of Formula I Starting from Intermediates of Formula VI and III:

By copper-catalyzed coupling of ortho-dihalo intermediate VI and a primary amide (III, $Y_2$=$CONH_2$). A copper catalyst such as CuI may be used in a solvent, such as toluene in the presence of base at elevated temperatures. (Altenhoff et al. Adv. Synth. Catal. 2004, 346, 1661).

Methods of Preparation of Labeled Compounds of Formula Ia

In general, the same synthetic reactions used for the assembly of non-labeled compounds of formula Ia from non-labeled reagents or intermediates, can be employed for the analogous incorporation of a detectable isotope by use of the corresponding labeled reagents or intermediates.

It is preferred to introduce the label at a late stage of the synthesis toward compounds of formula Ia, especially if the label is an isotope with relatively short half-life, such as $^{11}C$. Most preferred is to do this introduction as the last synthetic step. Several useful reagents, synthons or intermediates labeled with long-lived or non-radioactive isotopes, including for example $[^{2/3}H]H_2$, $[^{2/3}H]CH_3I$, $[^{13/14}C]CH_3I$, $[^{13/14}C]CN^-$, $[^{13/14}C]CO_2$ are commercially available and can, if needed, be further synthetically transformed by conventional synthetic methods. Reagents labeled with relatively more short-lived isotopes, such as $^{11}C$ and $^{18}F$, are generated by a cyclotron, followed by suitable trapping and optionally further synthetic manipulations to provide the desired reagent. The generation and the synthetic manipulations of labeled reagents and intermediates, and the use and chemistries of these precursors for the synthesis of more complex labeled molecules, is well known to the one skilled in the art of radio-synthesis and labeling and is reviewed in the literature (Långström et al. Acta Chem. Scand. 1999, 53, 651). For additional references see for example: Ali et al. Synthesis 1996, 423 for labeling with halogens; Antoni G., Kihlberg T., and Lęngström B. (2003) Handbook of nuclear chemistry, edited by Vertes A., Nagy S., and Klenscar Z., Vol. 4, 119-165 for labeling for PET-applications; Saljoughian et al. Synthesis 2002, 1781 for labeling with $^3$H; McCarthy et al. Curr. Pharm. Des. 2000, 6, 1057 for labeling with $^{14}$C.

Detectable isotopes, useful for the labeling of compounds of formula Ia as defined herein include, for use in PET: $^{11}$C, $^{18}$F, $^{75}$Br, $^{76}$Br and $^{120}$I, for use in SPECT: $^{123}$I and $^{131}$I, for MRI-applications: $^{19}$F and $^{13}$C, for detection in in-vitro and post-mortem samples: $^3$H, $^{14}$C and $^{125}$I. The most useful isotopes for labeling are $^{11}$C, $^{18}$F, $^{123}$I, $^{19}$F, $^3$H and $^{14}$C.

Below follow non-limiting descriptions on processes for the preparation of labeled compounds of formula Ia:

Compounds of formula Ia and Ib, which carry a hydroxy-, amino- or aminoalkyl group are useful precursors for O- and N-alkylation, respectively, with a labeled alkylating agent, such as [$^{11}$C]methyl iodide or triflate, as described in for example Solbach et al. Applied Radiation and Isotopes 2005, 62, 591 and Mathis et al. J. Med. Chem. 2003, 46, 2740, or [$^3$H]-methyl iodide, or [$^{14}$C]-methyl iodide.

For example, the compounds of formula Ia, in which one of R1 and R2 is hydroxy (the other is hydrogen), or compounds of formula Ib, in which one of R8 and R11 is hydroxy (the other is hydrogen), or constitute precursors for labeling. When such a precursor is treated with [$^{11}$C]methyl iodide under basic condition, such as in the presence of potassium carbonate, in a solvent such as DMSO, selective O-alkylation occurs in the presence of N-nucleophiles, such as amino or aminomethyl, because of relatively higher reactivity of the oxygen-atom after deprotonation, and thus in the formation of compounds of formula Ia and Ib in which the OH-group has been transformed into the O[$^{11}$C]CH$_3$-group. Compounds of formula Ib in which R8 or R11 is a protected (e.g. with TBDMS) hydroxy group, X$_8$ is N, and R10 is hydroxy, are useful precursors for labeling through O-alkylation by use of $^{11}$C-methyl iodide in the presence of Ag$_2$CO$_3$ as a base (Shinzo K. Synth Comm 2006, 36, 1235).

The most preferred precursors for labeling by selective introduction of a $^{11}$C-methyl group by N-alkylation, are compounds in which the reactivity to alkylation, of a present competing nucleophilic functional group, such as hydroxy or an aromatic N—H functionality, is lowered or blocked by a suitable protective group. The function of the protective group is, in this context, to protect the nucleophilic functional group from alkylation and should preferrably be stable under non-aqueous basic conditions, under which the desired N-alkylation is facilitated, but readily removed by other means after fulfillment of its duty. Such protective groups, and methods for their introduction and removal, are well known to the one skilled in the art. Examples of protective groups useful for protection of aromatic hydroxy-groups against competing alkylation include, but is not limited to, methyl, 2-(trimethylsilyl)ethoxymethyl, alkoxymethyl and t-butyldimethylsilyl. Removal of such a protective group after the alkylation is well known to the one skilled in the art and include, in the case of silyl-based protective groups such as t-butyldimethylsilyl, for example treatment with a fluoride ion source, such as TBAF, or treatment with water under basic conditions, in a suitable solvent, such as DMSO in the presence of KOH at rt. Examples of protective groups useful for protection of an aromatic N—H functionality against competing alkylation include, but is not limited to, SO$_2$N(CH$_3$)$_2$, SO$_2$(p-methyl)phenyl, CO$_2$CH$_2$CCl$_3$, CO$_2$(CH$_2$)$_2$Si(CH$_3$)$_2$, t-butyldimethylsilyl and P(=S)phenyl$_2$. In the case where an aromatic hydroxy-functionality, and an aromatic N—H functionality, are simultaneously protected against alkylation, it is preferred to use one protective group, such as t-butyldimethylsilyl, or two different protective groups, which allow simultaneous de-protection of both functionalities in one laboratory step by employment of one de-protection reagent.

Compounds of formula Ia or Ib, carrying an aromatic amino-group, are useful precursor for labeling by initial diazotation (i.e. transformation of the amino-group into the N$_2^+$ moiety), when appropriate, followed by conversion into the corresponding triazine derivative before subsequent treatment with labeled nucleophilic reagents according to standard reactions. Detectable isotopes that may be introduced this way include, but is not limited to $^{18}$F, $^{75}$Br, $^{123}$I, $^{125}$I and $^{131}$I as described in for example Zhu et al J. Org. Chem. 2002, 67, 943; Maeda et al. J. Label Compd Radiopharm 1985, 22, 487; Berridge et al. J. Label Compd Radiopharm 1985, 22, 687; Suehiro et al. J. Label Compd Radiopharm 1987, 24, 1143; Strouphauer et al. Int. J. Appl. Radiat. Isot. 1984, 35, 787; Kortylevicz et al. J. Label Compd Radiopharm 1994, 34, 1129; Khalaj et al. J. Label Compd Radiopharm 2001, 44, 235 and Rzeczotarski et al. J. Med. Chem. 1984, 27, 156.

In compounds of formula Ib, carrying an aromatic trialkyltin-group, halogenation with labeled reagents results in displacement of the trialkyltin-group as described in for example Staelens et al. J. Label Compd Radiopharm 2005, 48, 101; Hocke et al. Bioorg. Med. Chem. Lett. 2004, 14, 3963; Zhuang et al. J. Med. Chem. 2003, 46, 237; Füchtner et al. Appl. Rad. Isot. 2003, 58, 575 and Kao et al. J. Label Compd Radiopharm 2001, 44, 889. The same precursors are also useful for palladium-catalyzed conversion into the corresponding $^{11}$C-labeled ketones and methyl-derivatives as described in for example Lidström et al. J. Chem. Soc. Perkin Trans. 1 1997, 2701 and Tarkiainen et al. J. Label Compd Radiopharm 2001, 44, 1013. The trialkyltin substituted compounds, in turn, are preferably prepared from the corresponding halides or pseudo-halides, such as the triflates, by well known methods employing palladium as catalyst in reaction with the corresponding distannane. When this methodology is used, the trialkyltin-group is preferably trimethyltin or tributyltin.

Compounds of formula Ib, which are carrying an aromatic trialkyltin group, preferably n-Bu$_3$Sn, X6 is carbon, X7 or X8 is nitrogen (the other is carbon), and R10 is methylamino, dimethylamino or methoxy, are suitable precursors for labeling with $^{123}$I or $^{125}$I by iododestannylation under oxidative conditions in the presence of labelled iodide according to the method described in, for example, in Zhuang et al. Nucl. Med. Biol. 2001, 28, 887. When any one of the heterocyclic substituents in a precursor, is a leaving group suitable for nucleophilic aromatic substitution, a labeled nucleophile, such as a halogenide or cyanide, can be introduced by such a displacement resulting in a labeled compound of formula Ia, as described in for example Zhang et al. Appl. Rad. Isot. 2002, 57, 145. The aromatic ring on which the displacement takes place is preferably relatively electron-poor for a facile reaction, and might therefore need to be substituted with an electron-withdrawing activating group such as cyano, carbaldehyde or nitro. Useful reactions, closely related to nucleophilic aromatic substitutions and well known to the one skilled in the art, include the employment of stochiometric amounts of copper-salts for the introduction of a labeled iodo-atom, and the use of palladium-catalysis for the introduction of a $^{11}$C-labelled cyano-group, as described in for example Musacio et al. J. Label Compd Radiopharm 1997, 34, 39 and Andersson et al. J. Label Compd Radiopharm 1998, 41, 567 respectively. Also, an $^{18}$F-atom may be introduced, for example by use of K[$^{18}$F]-K$_{222}$ in DMSO under microwave irradiation as described in Karramkam, M. et al. J. Labelled Compd. Rad. is 2003, 46, 979. If the aromatic ring onto which the leaving group is positioned is more electron-deficient as compared to benzene, such as in 2-halo pyridines and pyrimidines, it is generally not needed to employ activating groups for electrophilic aromatic substitution to take place.

Compounds of formula Ia, where Q is Q1, and Ib, where R3 and R10, respectively, are either of the leaving-groups fluoro, chloro, bromo, iodo, or a sulphonate ester, and either or both of X2 and X4, and X6 and X8 is nitrogen, are suitable precursors for labeling via nucleophilic aromatic substitution. It is furthermore preferable to use a leaving group that is chemically diverse from the group introduced by the reaction with the labeled nucleophile in order to facilitate chromatographic separation of the labeled reaction product from the unconsumed precursor.

Compounds of formula Ib, in which R8 or R11 is a protected (e.g. TBDMS) hydroxy group (the other is hydrogen), and R10 is $O(CH_2)_2OTos$ or $NH(CH_2)_2OTos$, are useful precursors for labeling with fluorine by use of either kryptofix 2.2.2-[$^{18}$F]fluoride complex (Schirrmacher et al. J. Labelled Compd. Rad. 2001, 44, 627), or tetrabutylammonium [$^{18}$F] fluoride in $CH_3CN$ under heating (Hamacher et al. Appl. Radiat. Isotopes 2002, 57, 853), as sources of nucleophilic $^{18}$F for nucleophilic replacement of the formal leaving group $OTos^-$. Other suitable leaving groups that may be employed are well known to the one skilled in the art and include, but is not limited to bromo, iodo, $OSO_2CF_3$, $OSO_2CH_3$ and $OSO_2phenyl$.

Additional useful methods, well known to the one skilled in the art, for preparation of labeled compounds of formula Ia by functional group transformations of suitable precursors include N-acylation of amines with [$^{11}$C], [$^{14}$C], or [$^{3}$H]acyl chlorides, palladium-catalyzed [$^{11}$C] or [$^{14}$C] cyanation of aromatic chlorides, bromides or iodides, transition-metal catalyzed substitution of suitable halides for $^3H$ in the presence of [$^3$H]$H_2$, and palladium-catalyzed carbonylations with [$^{11/14}$C]CO (Perry et al. Organometallics 1994, 13, 3346).

COMPOUND EXAMPLES

Below follows a number of non-limiting examples of compounds of the invention.

General Methods

All solvents used were commercially available analytical grade anhydrous solvents. Reactions were typically run under an inert atmosphere of nitrogen or argon.

$^1$H spectra were recorded on a Bruker av400 NMR spectrometer, operating at 400 MHz for proton, equipped with a 3 mm flow injection SEI $^1$H/D-$^{13}$C probehead with Z-gradients, using a BEST 215 liquid handler for sample injection, or on a Bruker DPX400 NMR spectrometer, operating at 400 MHz for proton, equipped with a 5 mm 4-nucleus probehead equipped with Z-gradients.

Unless specifically noted in the examples, $^1$H spectra were recorded at 400 MHz in DMSO-$d_6$ as solvent. The residual solvent signal was used as reference. The following reference signals were used: the middle line of DMSO-$d_6$ δ 2.50; the middle line of $CD_3OD$ δ 3.31; $CDCl_3$ δ 7.26. In those instances where spectra were run in a mixture of $CDCl_3$ and $CD_3OD$, the reference was set to 3.31 ppm. All chemical shifts are in ppm on the delta-scale (δ) and the fine splitting of the signals as appearing in the recordings (s: singlet, d: doublet, t: triplet, q: quartet, m: multiplet, br: broad signal).

$^3$H spectra were recorded on a Bruker DRX600 NMR Spectrometer, operating at 640 MHz for tritium and at 600 MHz for proton, equipped with a 5 mm $^3$H/$^1$H SEX probehead with Z-gradients. $^1$H decoupled $^3$H spectra were recorded on samples dissolved in $CD_3OD$. For $^3$H NMR spectra referencing, a ghost reference frequency was used, as calculated by multiplying the frequency of internal TMS in a $^1$H spectrum with the Larmor frequency ratio between $^3$H and $^1$H (1.06663975), according to the description in Al-Rawi et al. J. Chem. Soc. Perkin Trans. II 1974, 1635.

Mass spectra were recorded on a Waters LCMS consisting of an Alliance 2795 or Acquity system (LC), Waters PDA 2996, and ELS detector (Sedex 75) and a ZMD single quadrupole or ZQ mass spectrometer. The mass spectrometer was equipped with an electrospray ion source (ES) operated in a positive or negative ion mode. The capillary voltage was 3 kV and cone voltage was 30 V. The mass spectrometer was scanned between m/z 100-600 with a scan time of 0.7 s. The column temperature was set to 40° C. (Alliance) or 65° C. (Acquity). A linear gradient was applied starting at 100% A (A: 10 mM $NH_4OAc$ in 5% MeCN) and ending at 100% B (B: MeCN). The column used was a X-Terra MS C8, 3.0×50; 3.5 μm (Waters) run at 1.0 mL/min (Alliance), or an Acquity UPLC™ BEH $C_8$ 1.7 μm 2.1×50 mm run at 1.2 mL/min.

Preparative chromatography (prep. HPLC) was run on either of two Waters autopurification HPLCs: (1) equipped with a diode array detector and an XTerra MS C8 column, 19×300 mm, 10 μm. (2) consisting of a ZQ mass spectrometer detector run with ESI in positive mode at a capillary voltage of 3 kV and a cone voltage of 30 V, using mixed triggering, UV and MS signal, to determine the fraction collection. Column: XBridge™ Prep C8 5 μm OBDT 19×100 mm. Gradients with MeCN/(95:5 0.1M $NH_4QAc$:MeCN) were used at a flow rate of 20 or 25 mL/min.

Microwave heating was performed in a Creator, Initiator or Smith Synthesizer Single-mode microwave cavity producing continuous irradiation at 2450 MHz.

Below follows a number of non-limiting examples of compounds of the invention. All of the below exemplified compounds, or their corresponding non-labeled analogs, which are not solely precursors and thus indicated to be such, display an $IC_{50}$ of less than 20 μM in the competition binding assay described herein.

Example 1

5-(6-Methoxy-1,3-benzoxazol-2-yl)-N,N-dimethylpyridin-2-amine

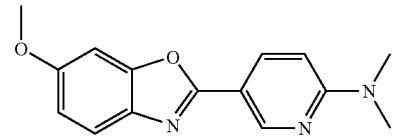

(a)
6-Chloro-N-(2-hydroxy-4-methoxyphenyl)nicotinamide

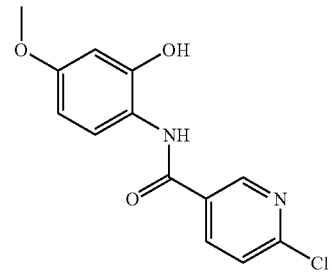

6-Chloronicotinyl chloride (2.0 g, 11.4 mmol) in THF (10 mL) was added dropwise to a mixture of 2-hydroxy-4-methoxyaniline (1.58 g) and triethylamine (1.8 mL) in THF (20 mL) at r.t. The reaction was stirred at r.t for 30 minutes and was then heated to reflux for 5 minutes. After cooling to r.t. the solid was collected, rinsed with water, dried (under vacuum over P$_2$O$_5$), to give the title compound (1.77 g) as an orange solid. $^1$H NMR δ ppm 9.78 (br. s, 1H) 9.63 (br. s, 1H) 8.94 (d, 1H) 8.34 (dd, 1H) 7.68 (d, 1H) 7.34 (d, 1H) 6.49 (d, 1H) 6.42 (dd, 1H) 3.71 (s, 3H); MS m/z (M+H) 279, 281; (M−H) 277, 279.

(b) 5-(6-Methoxy-1,3-benzoxazol-2-yl)-N,N-dimethylpyridin-2-amine (Final Compound)

6-Chloro-N-(2-hydroxy-4-methoxyphenyl)nicotinamide (40 mg, 0.14 mmol) was dissolved in DMF (1.5 mL) and one drop of sulfuric acid was added. The reaction was run at 230° C. for 20 minutes in a microwave reactor. The mixture was added to water, the solid was collected, rinsed with water and dried. The crude product was purified by flash column chromatography using 40% ethyl acetate in hexane, giving the title compound (14 mg) as an orange solid. $^1$H NMR (400 MHz, CHLOROFORM-d) δ ppm 8.96 (d, 1H) 8.19 (dd, 1 H) 7.57 (d, 1H) 7.10 (d, 1H) 6.92 (dd, 1H) 6.60 (d, 1H) 3.88 (s, 3H) 3.20 (s, 6H); MS m/z (M+H) 270.

Example 2

2-[6-(Dimethylamino)pyridin-3-yl]-1,3-benzoxazol-6-ol

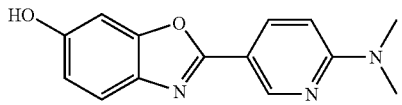

5-(6-Methoxy-1,3-benzoxazol-2-yl)-N,N-dimethylpyridin-2-amine (31 mg, 0.12 mmol) was mixed with hydrogen bromide (48% aq., 2 mL) and a crystal of tetrabutylammonium bromide was added. The reaction was run at 120° C. for 5 minutes in a microwave reactor. The reaction mixture was added to sodium bicarbonate (sat. aq.) and the solid was collected. The solid was then dissolved in CH$_2$Cl$_2$/ethyl acetate, dried (MgSO$_4$), filtered and evaporated in vacuo, giving the title compound (6 mg) as a purple solid. $^1$H NMR (400 MHz, CD$_3$OD) δ ppm 8.83 (d, 1H) 8.17 (dd, 1H) 7.44 (d, 1H) 7.02 (d, 1H) 6.75-6.88 (m, 2H) 3.19 (s, 6H); MS m/z (M+H) 256; (M−H) 254.

Example 3

5-(6-Methoxy-1,3-benzoxazol-2-yl)-N-methylpyridin-2-amine

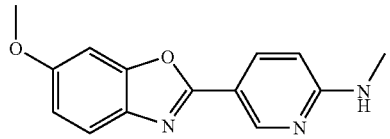

(a) N-(2-Hydroxy-4-methoxyphenyl)-6-(methylamino)nicotinamide

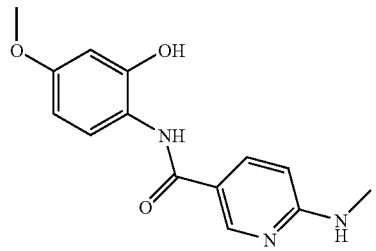

6-Chloro-N-(2-hydroxy-4-methoxyphenyl)nicotinamide (0.40 g, 1.44 mol) was mixed with a solution of 8M methylamine in methanol (4 mL) and heated in a microwave reactor at 250° C. for 10 minutes. The solvent was evaporated in vacuo and the residue was partitioned between water and ethyl acetate. The aqueous layer was extracted five timed with ethyl acetate The pooled organics were dried (MgSO$_4$), filtered and evaporated. The solid was titurated with CH$_2$Cl$_2$, filtered and dried, giving the title compound (0.25 g) as a solid. $^1$H NMR δ ppm 9.73 (s, 1H) 9.38 (s, 1H) 8.65 (d, 1H) 7.92 (dd, 1H) 7.33 (d, 1H) 7.16 (d, 1H) 6.24-6.58 (m, 3H) 3.70 (s, 3H) 2.83 (d, 3H); MS m/z (M+H) 274; (M−H) 272.

(b) 5-(6-Methoxy-1,3-benzoxazol-2-yl)-N-methylpyridin-2-amine (Final Compound)

N-(2-Hydroxy-4-methoxyphenyl)-6-(methylamino)nicotinamide (0.23 g, 0.84 mmol) was mixed with acetic acid (4 mL) and the reaction was run in a microwave reactor at 200° C. for 25 minutes. The reaction mixture was added to water and made basic with sodium bicarbonate (sat. aq.). The aqueous solution was extracted three times with diethyl ether and the combined organic layers were washed with brine, dried (MgSO$_4$) and evaporated. The crude product was purified first by flash column chromatography (hexane/ethyl acetate-gradient; 30-50% ethyl acetate), followed by preparative HPLC, resulting in the isolation of N-[5-(6-methoxy-1,3-benzoxazol-2-yl)pyridin-2-yl]-N-methylacetamide (6 mg) as a minor product, together with the title compound (0.13 g) as a solid. $^1$H NMR (400 MHz, CHLOROFORM-d) δ ppm 8.90 (d, 1H) 8.23 (dd, 1H) 7.59 (d, 1H) 7.10 (d, 1H) 6.94 (dd, 1H) 6.52 (d, 1H) 5.26 (br. s, 1H) 3.89 (s, 3H) 2.82-3.16 (m, 3 H); MS m/z (M+H) 256.

Example 4

N-[5-(6-Methoxy-1,3-benzoxazol-2-yl)pyridin-2-yl]-N-methylacetamide

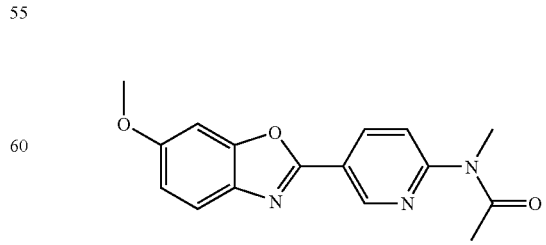

The title compound (6 mg) was isolated from the crude mixture obtained in the preparation of 5-(6-methoxy-1,3- benzoxazol-2-yl)-N-methylpyridin-2-amine. ¹H NMR (400 MHz, CHLOROFORM-d) δ ppm 9.24 (d, 1H) 8.47 (dd, 1H) 7.66 (d, 1H) 7.62 (d, 1H) 7.14 (d, 1H) 7.00 (dd, 1H) 3.91 (s, 3H) 3.50 (s, 3H) 2.27 (s, 3H); MS m/z (M+H) 298.

Example 5

2-[6-(Methylamino)pyridin-3-yl]-1,3-benzoxazol-6-ol

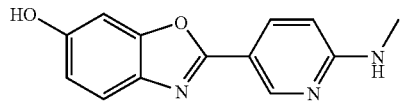

5-(6-Methoxy-1,3-benzoxazol-2-yl)-N-methylpyridin-2-amine (50 mg, 0.20 mmol) was dissolved in CH$_2$Cl$_2$ (10 mL) and made acidic with 2M HCl in diethylether. The solvent was removed in vacuo and hydrogen bromide (48% aq., 2 mL) was added. The reaction was run in a microwave reactor at 120° C. for 15 minutes. The mixture was then made basic with sodium bicarbonate and extracted twice with ethyl acetate. The combined organic layers were washed with brine, dried (MgSO$_4$), filtered and evaporated in vacuo. The crude product was purified by preparative HPLC, to give the title compound (11 mg) as a white solid. ¹H NMR δ ppm 9.95 (br. s, 1H) 8.72 (d, 1H) 7.99 (dd, 1H) 7.46 (d, 1 H) 7.28 (d, 1 H) 7.03 (d, 1H) 6.79 (dd, 1H) 6.58 (d, 1H) 2.85 (d, 3H); MS m/z (M+H) 242, (M−H) 240.

Example 6

[N-Methyl-³H$_3$]-[5-(6-Methoxy-benzooxazol-2-yl)-pyridin-2-yl]-dimethyl-amine

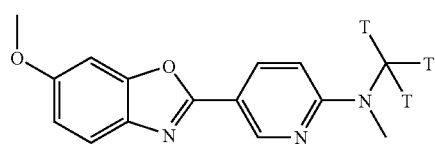

5-(6-Methoxy-1,3-benzoxazol-2-yl)-N-methylpyridin-2-amine (1.5 mg, 6 µmol) was mixed with [³H]methyl iodide (75 mCi, 0.6 µmol) in DMF (0.5 mL) with sodium hydride (2 mg, 80 µmol) as base and heated to 60° C. for 1.5 h. The reaction mixture was purified by reversed phase HPLC to afford the title compound (70 mCi, 93%). MS m/z (M+H) 276; ³H NMR (CD$_3$OD) 3.13 (s, CT$_3$).

Example 7

[N-Methyl-³H$_3$]-2-(6-Dimethylamino-pyridin-3-yl)-benzooxazol-6-ol

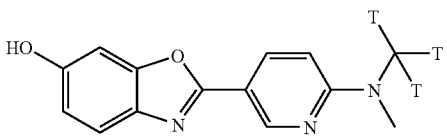

[N-Methyl-³H$_3$]-[5-(6-Methoxy-benzooxazol-2-yl)-pyridin-2-yl]-dimethyl-amine (50 mCi) was mixed with sodium thiophenoxide (17 mg, 130 µmol) in NMP (0.4 mL) and heated to 250° C. for 60 min by means of a microwave reactor. The reaction mixture was purified by reversed phase HPLC to afford the title compound (35 mCi, 76%). MS m/z (M+H) 262; ³H NMR ³H NMR (CD$_3$OD) 3.12 (s, CT$_3$).

Example 8

[O-Methyl-³H$_3$]-[5-(6-Methoxy-benzooxazol-2-yl)-pyridin-2-yl]-methyl-amine

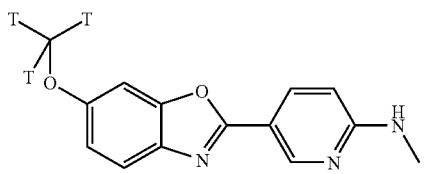

2-[6-(Methylamino)pyridin-3-yl]-1,3-benzoxazol-6-ol (1 mg, 6 µmol) was mixed with [³H]methyl iodide (75 mCi, 0.9 µmol) in DMF (0.5 mL) with sodium hydride (1.6 mg, 80 µmol) as base and heated to 70° C. for 40 min. The reaction mixture was purified by reversed phase HPLC to afford the title compound (6 mCi, 12%). MS m/z (M+H) 262.

Example 9

[N-Methyl-³H$_3$]-[5-(6-Methoxy-benzooxazol-2-yl)-pyridin-2-yl]-methyl-amine

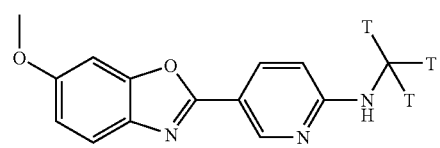

5-(6-Methoxy-1,3-benzoxazol-2-yl)-pyridin-2-amine (4.2 mg, 17 µmol) was mixed with [³H]methyl iodide (50 mCi, 0.6 µmol) in DMF (0.5 mL) with sodium hydride (3 mg) as base and heated to 60° C. for 1.0 h. The reaction mixture was purified by reversed phase HPLC to afford the title compound (22 mCi, 44%).

Example 10

[N-Methyl-$^3$H$_3$]-2-(6-Methylamino-pyridin-3-yl)-benzooxazol-6-ol

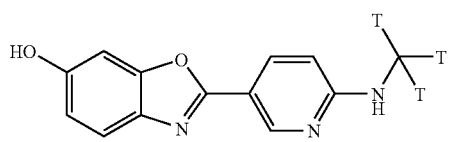

The product from the previous step ([N-Methyl-$^3$H$_3$]-[5-(6-Methoxy-benzooxazol-2-yl)-pyridin-2-yl]-methyl-amine) was mixed with sodium thiophenoxide (13 mg, 100 μmol) in NMP (0.4 mL) and heated to 250° C. for 30 min by means of a microwave reactor. The reaction mixture was purified by reversed phase HPLC to afford the title compound (18 mCi, 82%). MS m/z (M+H) 248.

Example 11

5-(5-Methoxy-1,3-benzoxazol-2-yl)-N,N-dimethylpyridin-2-amine

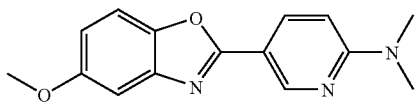

a) 6-(Dimethylamino)-N-(2-hydroxy-5-methoxyphenyl)nicotinamide

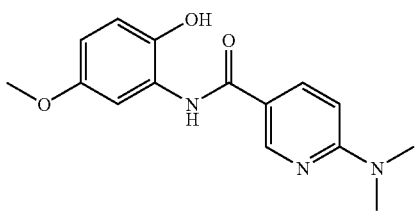

In three separate microwave reactor tubes were added 2-{[(6-fluoropyridin-3-yl)carbonyl]amino}-4-methoxyphenyl 6-fluoronicotinate (60.0 mg, 90.7 mg, 89.6 mg) and dimethylamine in water (40%, 2.5-3.0 mL). The tubes were heated in a microwave oven at 100° C. for 5 min. The three batches were combined and dimethylamine in water was removed in vacuo. The crude product was taken to the next step without further purification. MS m/z (M+H) 288.

b) 5-(5-Methoxy-1,3-benzoxazol-2-yl)-N,N-dimethylpyridin-2-amine

In two separate microwave reactor tubes, crude 6-(dimethylamino)-N-(2-hydroxy-5-methoxyphenyl)nicotinamide (3.0 mL) and acetic acid (6.0 mL) was mixed and heated in a microwave reactor at 190° C. for 10 min. The two batches were combined and the acetic acid was removed in vacuo. Dichloromethane and NaHCO$_3$ (sat. aq.) were added and the layers separated. The aqueous phase was extracted with dichloromethane (3×). The combined organic phases were dried (MgSO$_4$), filtered and the solvent removed in vacuo. The crude material was purified by flash chromatography (SiO$_2$; heptane/EtOAc 60/40) to afford 104.4 mg (62% in two steps) of the product as a white solid. $^1$H NMR δ ppm 8.85 (d, 1H), 8.15 (dd, 1H), 7.60 (d, 1H), 7.27 (d, 1H), 6.92 (dd, 1H), 6.81 (d, 1H), 3.81 (s, 3 H), 3.14 (s, 6H). MS m/z (M+H) 270.

Example 12

2-[6-(Dimethylamino)pyridin-3-yl]-1,3-benzoxazol-5-ol

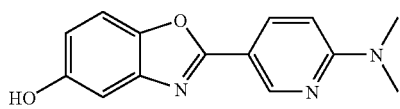

To a solution of 5-(5-methoxy-1,3-benzoxazol-2-yl)-N,N-dimethylpyridin-2-amine (0.368 mmol) in dichloromethane (2.0 mL) was added BBr$_3$ in dichloromethane (1.84 mmol) at 0° C. under an atmosphere of argon and the reaction stirred for 1 h at 0° C. The reaction mixture was neutralized with NaHCO$_3$ (sat. aq.) and dichloromethane was added. The layers were separated and the aqueous phase was extracted with dichloromethane (4×). The combined organic phases were dried (MgSO$_4$), filtered and the solvents removed in vacuo. The crude material was purified by preparative HPLC to give 22.3 mg of the title compound as a white solid. $^1$H NMR δ ppm 9.44 (s, 1H), 8.83 (d, 1H), 8.13 (dd, 1H), 7.48 (d, 1H), 7.01 (d, 1H), 6.80 (d, 1H), 6.76 (dd, 1H), 3.14 (s, 6H). MS m/z (M+H) 256.

Example 13

5-(6-Methoxy-1,3-benzoxazol-2-yl)-N,N-dimethylpyrimidin-2-amine

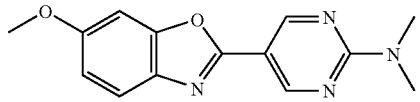

6-Methoxy-1,3-benzoxazole (0.67 mmol), 5-bromo-N,N-dimethylpyrimidin-2-amine (0.80 mmol), CuBr (0.13 mmol), Cs$_2$CO$_3$ (0.67 mmol) and Pd(t-Bu$_3$P)$_2$ (0.067 mmol) in dry DMF (3 ml) was stirred 30 min at 160° C. in a microwave reactor. The reaction mixture was filtered through celite, washed through with CH$_2$Cl$_2$ and the solvents were removed under reduced pressure. The crude product was purified by flash chromatography (CH$_2$Cl$_2$/CH$_2$Cl$_2$/MeOH (9:1) gradient) to give the title compound as an off white solid (108.2 mg). $^1$H NMR δ ppm 8.99 (s, 2H) 7.62 (d, 1H) 7.38 (d, 1H) 6.98 (dd, 1H) 3.83 (s, 3H) 3.23 (s, 6H); MS m/z 271 (M+H).

Example 14

2-[2-(Dimethylamino)pyrimidin-5-yl]-1,3-benzoxazol-6-ol

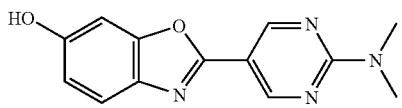

The title compound was synthesized from 5-(6-Methoxy-1,3-benzoxazol-2-yl)-N,N-dimethylpyrimidin-2-amine according to the general procedure as described for 2-[6-(dimethylamino)pyridin-3-yl]-1,3-benzoxazol-5-ol to give 30.3 mg: $^1$H NMR δ ppm 9.85 (br. s, 1H) 8.97 (s, 2H) 7.51 (d, 1H) 7.05 (d, 1H) 6.82 (dd, 1H) 3.22 (s, 6 H); MS m/z 257 (M+H).

Example 15

2-(6-Bromopyridin-3-yl)-6-methoxy-1,3-benzoxazole

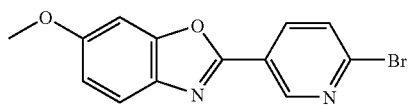

A solution of 2-hydroxy-4-methoxy-aniline hydrochloride (1.13 mmol) and triethylamine (167 μL) in dry methanol was treated with 2-bromo-5-formylpyridine (1.13 mmol). The resulting mixture was stirred at r.t. over night and then concentrated to dryness. The residue was separated between CH$_2$Cl$_2$ and brine and the aqueous layer extracted (2×) with CH$_2$Cl$_2$, the combined organics were dried with Na$_2$SO$_4$, filtered and evaporated to give 314.9 mg of the corresponding crude imine as a dark red solid. MS m/z 307, 309 (M+H, Bromo isotopes). The residue was taken up in CH$_2$Cl$_2$ (10 mL) and DDQ (255 mg, 1.1 eq) was added. After stirring at room temperature for 45 min, the resulting mixture was diluted with CH$_2$Cl$_2$ (10 mL) and washed sequentially with saturated Na$_2$CO$_3$ (2×10 mL) and brine (10 mL). The organic layer was dried with Na$_2$SO$_4$ and evaporated to give 620 mg of a brown solid. The crude was purified by flash column chromatography (Heptane:EtOAc, 0 to 100%) to give the title compound as a white solid (159.6 mg). $^1$H NMR δ ppm 9.05-9.11 (m, 1H) 8.38 (dd, 1H) 7.90 (dd, 1H) 7.74 (d, 1H) 7.46 (d, 1H) 7.05 (dd, 1 H) 3.86 (s, 3H); MS m/z 305, 307 (M+H, Bromo isotopes).

Example 16

2-[6-(2-Fluoroethoxy)pyridin-3-yl]-6-methoxy-1,3-benzoxazole

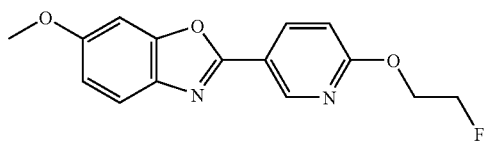

Toluene (1 mL) was added to Pd(OAc)$_2$ (6.4 μmol), 2-(di-t-butylphosphino)-1,1'-binaphtyl (racemic, 8.0 μmol), Cs$_2$CO$_3$ (0.24 mmol) and 2-(6-bromopyridin-3-yl)-6-methoxy-1,3-benzoxazole under Ar. 2-Fluoroethanol (0.16 mmol) was added and the reaction was stirred 1 h at 120° C. Additional Pd(OAc)$_2$ (8.0 μmol), 2-(di-t-butylphosphino)-1,1'-binaphtyl (racemic, 8.0 μmol) and 2-fluoroethanol (0.16 mmol) was added and the mixture was again stirred 1 h at 120° C. The reaction mixture was cooled to r.t., diluted with EtOAc, filtered through celite and concentrated. The crude product was subjected to reverse phase HPLC to afford the title compound as an off white solid (10.1 mg). $^1$H NMR (400 MHz, Chloroform-d) δ ppm 8.95 (d, 1H) 8.36 (dd, 1H) 7.62 (d, 1H) 7.12 (d, 1H) 6.91-6.99 (m, 2H) 4.82-4.88 (m, 1H) 4.69-4.76 (m, 2H) 4.61-4.66 (m, 1H) 3.89 (s, 3 H); MS m/z (M+H) 289.

Example 17

2-(5-Bromopyridin-2-yl)-6-methoxy-1,3-benzoxazole

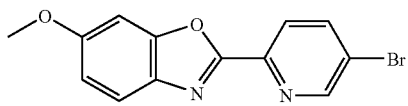

The title compound was synthesized according to a procedure similar to that as described for 2-(6-bromopyridin-3-yl)-6-methoxy-1,3-benzoxazole starting from 3-bromo-6-formylpyridine to give 578.1 mg as an off white solid: 1H NMR δ ppm 8.91 (dd, 1H) 8.26-8.32 (m, 1H) 8.20 (dd, 1H) 7.75 (d, 1H) 7.46 (d, 1H) 7.06 (dd, 1H) 3.86 (s, 3 H); MS m/z 305, 307 (M+H, Bromo isotopes).

Example 18

5-(6-methoxy-1,3-benzoxazol-2-yl)pyridin-2-amine

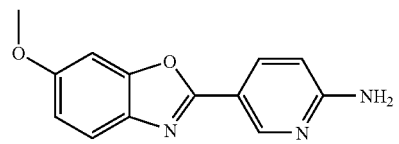

2-Bromo-6-methoxy-1,3-benzoxazole (0.877 mmol), 2-amino-5-(4,4,5,5-tetramethyl-[1,3,2]dioxaborolan-2-yl)-pyridine (1.3 mmol), K$_2$CO$_3$ 2M aq. (3.5 mmol) and Pd(dppf)Cl$_2$ (0.022 mmol) were mixed in DMF (5 ml) and stirred at 80° C. for 2 h. The solvents were evaporated under reduced pressure and the crude product was subjected to flash column chromatography followed by purification using reverse phase HPLC to afford the title compound as a white solid (68 mg). $^1$H NMR δ ppm 8.67 (br. s, 1H) 8.12-7.91 (m, 1H) 7.69-7.51 (m, 1H) 7.34 (br. s, 1H) 6.89-7.00 (m, 1H) 6.75 (br. s, 2H) 6.43-6.65 (m, 1H) 3.84 (s, 3H); MS m/z 242 (M+H).

Example 19

N-(2-fluoroethyl)-5-(6-methoxy-1,3-benzoxazol-2-yl)pyridin-2-amine

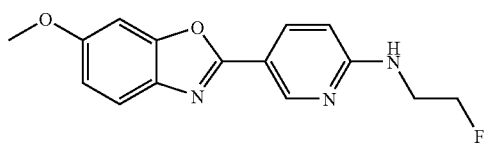

a) tert-Butyl [5-(6-methoxy-1,3-benzoxazol-2-yl)pyridin-2-yl]carbamate

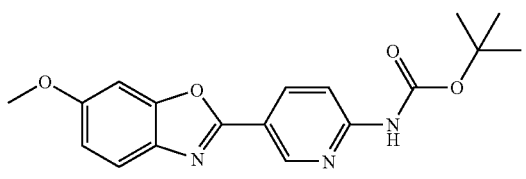

5-(6-Methoxy-1,3-benzoxazol-2-yl)pyridin-2-amine (1.95 mmol) and di-tert-butyl dicarbonate (2.33 mmol) was dissolved in THF (30 mL) cooled with an icebath. NHMDS (1M in THF, 2.33 mmol) was added slowly and the reaction was allowed to warm to r.t. The reaction mixture was stirred at r.t. for 2 h and the solvent was removed under reduced pressure. EtOAc and NaHCO$_3$ (sat. aq.) were added and the layers separated, the organic layer was washed with brine, dried (Na$_2$SO$_4$), filtered and concentrated. The crude product was purified by flash chromatography (Heptane/EtOH, gradient 0:100) to give 225 mg. MS m/z 342 (M+H).

b) tert-butyl (2-fluoroethyl)[5-(6-methoxy-1,3-benzoxazol-2-yl)pyridin-2-yl]carbamate

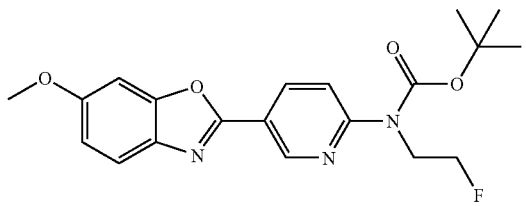

tert-Butyl [5-(6-methoxy-1,3-benzoxazol-2-yl)pyridin-2-yl]carbamate (0.65 mmol) and sodium hydride (0.78 mmol) were dissolved in dry DMF (20 mL) at 0° C. After 5 min 1-bromo-2-fluoroethane (0.72 mmol) was added and the reaction was allowed to warm to r.t. After 2 h additional sodium hydride and 1-bromo-2-fluoroethane was added and the reaction mixture was stirred over night. The solvent was removed under reduced pressure and redissolved in EtOAc. Water was added and the layers separated. The aqueous layer was extracted with EtOAc (2×), dried (Na$_2$SO$_4$) and evaporated to give 253 mg as brown oil. The crude product was taken to the next step without further purification. MS m/z 388 (M+H).

c) N-(2-fluoroethyl)-5-(6-methoxy-1,3-benzoxazol-2-yl)pyridin-2-amine tert-Butyl (2-fluoroethyl)[5-(6-methoxy-1,3-benzoxazol-2-yl)pyridin-2-yl]carbamate (0.65 mmol) was dissolved in CH$_2$Cl$_2$ (20 mL), trifluoroacetic acid (0.5 mL) was added and the reaction mixture was stirred for 4 hours at r.t. Water (20 mL), NaOH (1.5 mL, 5M aq., pH adjusted to 12) and CH$_2$Cl$_2$ (20 mL) was added and the layers separated. The aqueous layer was extracted with CH$_2$Cl$_2$ (3×). The combined organic layers were dried (Na$_2$SO$_4$) filtered and concentrated. Purification using reverse phase HPLC afforded the title compound (78.0 mg). 1H NMR δ ppm 8.74 (d, 1H) 8.03 (dd, 1H) 7.60-7.64 (m, 1H) 7.58 (d, 1H) 7.35 (d, 1H) 6.95 (dd, 1H) 6.70 (d, 1H) 4.60-4.66 (m, 1H) 4.47-4.54 (m, 1H) 3.82 (s, 3H) 3.67-3.74 (m, 1H) 3.60-3.67 (m, 1H); ESI-MS m/z 288 (M+H).

Example 20

5-(6-Methoxy-1,3-benzoxazol-2-yl)pyrimidin-2-amine

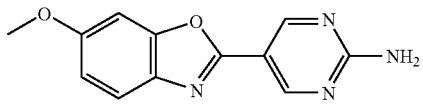

The title compound was synthesised according to the procedure described for 5-(6-methoxy-1,3-benzoxazol-2-yl)pyridin-2-amine starting from 2-aminopyrimidine-5-boronic acid pinacol ester. $^1$H NMR δ ppm 8.89 (s, 2H) 7.61 (d, 1H) 7.48 (s, 2H) 7.37 (d, 1 H) 6.97 (dd, 1H) 3.83 (s, 3H); MS m/z 243 (M+H).

Example 21

N-(2-fluoroethyl)-5-(6-methoxy-1,3-benzoxazol-2-yl)pyrimidin-2-amine

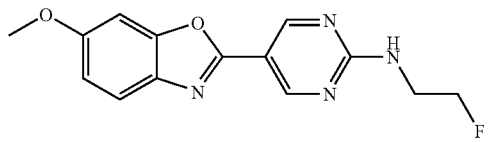

a) tert-Butyl [5-(6-methoxy-1,3-benzoxazol-2-yl)pyrimidin-2-yl]carbamate

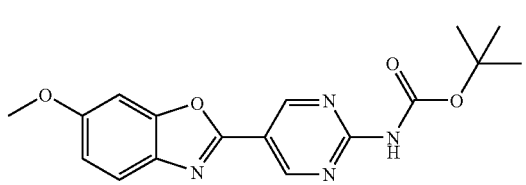

The title intermediate was synthesized from 5-(6-methoxy-1,3-benzoxazol-2-yl)pyrimidin-2-amine according to the procedure described for tert-butyl [5-(6-methoxy-1,3-benzoxazol-2-yl)pyridin-2-yl]carbamate to give 115 mg. $^1$H NMR 400 MHz, Chloroform-d) δ ppm 9.33 (s, 2H) 8.17 (s, 1H) 7.65 (d, 1H) 7.14 (d, 1H) 7.00 (dd, 1 H) 3.90 (s, 3H) 1.60 (s, 9H). MS m/z 343 (M+H).

b) tert-Butyl (2-fluoroethyl)[5-(6-methoxy-1,3-benzoxazol-2-yl)pyrimidin-2-yl]carbamate

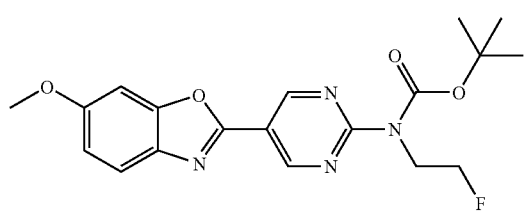

The title intermediate was synthesized from tert-butyl [5-(6-methoxy-1,3-benzoxazol-2-yl)pyrimidin-2-yl]carbamate according to the procedure described for tert-butyl (2-fluoroethyl)[5-(6-methoxy-1,3-benzoxazol-2-yl)pyridin-2-yl]carbamate to give 128 mg. ¹H NMR 400 MHz, Chloroform-d) δ ppm 9.33 (s, 2H) 7.66 (d, 1H) 7.14 (d, 1H) 7.00 (dd, 1H) 4.79 (t, 1H) 4.67 (t, 1H) 4.42 (t, 1H) 4.37 (t, 1H) 3.90 (s, 3 H) 1.57 (s, 9H) MS m/z 389 (M+H).

c) N-(2-fluoroethyl)-5-(6-methoxy-1,3-benzoxazol-2-yl)pyrimidin-2-amine

The title compound was synthesized from tert-butyl (2-fluoroethyl)[5-(6-methoxy-1,3-benzoxazol-2-yl)pyrimidin-2-yl]carbamate according to the procedure described for N-(2-fluoroethyl)-5-(6-methoxy-1,3-benzoxazol-2-yl)pyridin-2-amine to give 29.8 mg. MS m/z 289 (M+H).

Example 22

[N-Methyl-³H₃]-2-(2-Dimethylamino-pyrimidin-5-yl)-benzooxazol-6-ol

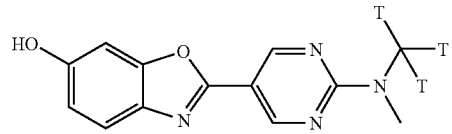

[5-(6-Methoxy-benzooxazol-2-yl)-pyrimidin-2-yl]-methyl-amine (2.2 mg, 8.6 μmol) was mixed with [³H]methyl iodide (50 mCi, 0.6 μmol) in dimethylformamide (0.4 mL) with sodium hydride as base and heated to 60° C. for 30 min. The reaction mixture was purified by reversed phase HPLC to afford [N-methyl-³H₃]-[5-(6-methoxy-benzooxazol-2-yl)-pyrimidin-2-yl]-dimethyl-amine. After evaporation the residue was mixed with sodium thiophenoxide (18 mg, 136 μmol) in N-methyl pyrrolidinone (0.4 mL) and heated to 250° C. for 30 min by means of a microwave reactor. The reaction mixture was purified by reversed phase HPLC to afford the title compound (44 mCi, 88%). MS m/z M+H 263; ³H NMR (proton decoupled in CD₃OD) 3.22 (s, CT₃).

Example 23

5-(6-Methoxy-1,3-benzoxazol-2-yl)-N-methylpyrimidin-2-amine

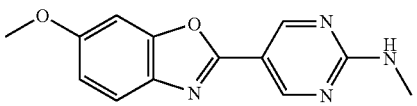

The title compound was synthesised according to the procedure described for 4-(6-methoxy-1,3-benzoxazol-2-yl)-N-methylaniline starting from 5-bromo-N-methylpyrimidin-2-amine. ¹H NMR δ ppm 8.84-9.02 (m, 2H) 7.95 (d, 1H) 7.61 (d, 1H) 7.37 (d, 1H) 6.97 (dd, 1 H) 3.83 (s, 3H) 2.89 (d, 3H); ES-MS m/z 257 (M+H).

Example 24

2-(6-Methoxypyridin-3-yl)-1,3-benzoxazol-6-ol

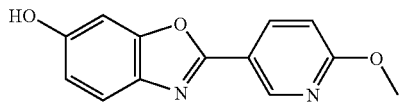

a) 4-{[(6-methoxypyridin-3-yl)methylene]amino}benzene-1,3-diol

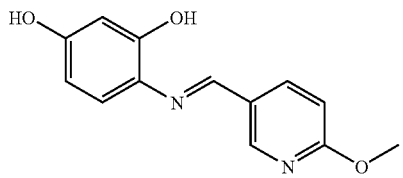

4-Aminoresorcinol hydrochloride (3.09 mmol) and triethylamine (3.25 mmol) were dissolved in dry methanol (20 mL). 6-Methoxynicotinaldehyde (3.09) was added and the mixture was stirred overnight. The solvents were removed under reduced pressure, the mixture diluted with EtOAc, washed with brine (2×), dried (Na₂SO₄), filtered and evaporated to give 1.31 g as a dark solid. The crude product was taken to the next step without further purification. MS m/z (M+H) 245.

b) 2-(6-Methoxypyridin-3-yl)-1,3-benzoxazol-6-ol

4-{[(6-methoxypyridin-3-yl)methylene]amino}benzene-1,3-diol was dissolved in CH₂Cl₂ (30 mL) and DDQ was added. The reaction mixture was stirred over night at r.t., SiO₂ was added and the solvents were removed under reduced pressure. The crude product was purified by flash column chromatography to give the title compound (189.1 mg). ¹H NMR δ ppm 9.88 (s, 1H) 8.90 (dd, 1H) 8.35 (dd, 1H) 7.56 (d, 1H) 7.09 (d, 1H) 6.85 (dd, 1H) 3.95 (s, 3H); MS m/z 243 (M+H).

Example 25

2-(6-morpholin-4-ylpyridin-3-yl)-1,3-benzoxazole

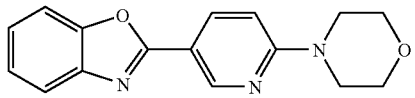

The title compound was synthesised according to the procedure described for 5-(6-methoxy-1,3-benzoxazol-2-yl)pyridin-2-amine starting from the boronate ester 4-(5-(4,4,5,5-tetramethyl-1,3,2-dioxaborolan-2-yl)pyridin-2-yl)-morpholine and 2-bromo-1,3-benzoxazole. ¹H NMR δ ppm 8.91 (d, 1H) 8.23 (dd, 1H) 7.71-7.76 (m, 2H) 7.37 (dd, 2 H) 7.03 (d, 1H) 3.69-3.73 (m, 4H) 3.62-3.66 (m, 4H); MS m/z 282 (M+H).

Example 26

6-methoxy-2-(6-methoxypyridin-3-yl)benzooxazole, 26-001

2-benzofuran-2-yl-6-methoxy-benzooxazole, 26-002 tert-butyl 5-methoxy-2-(6-methoxybenzooxazol-2-yl)indole-1-carboxylate, 26-003

2-(6-fluoro-5-methyl-pyridin-3-yl)-6-methoxy-benzooxazole, 26-004

2-(5-fluoro-6-methoxy-pyridin-3-yl)-6-methoxy-benzooxazole, 26-005

2-(1H-indol-5-yl)-6-methoxy-benzooxazole, 26-006

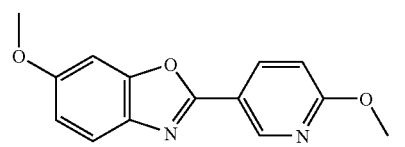
26-001

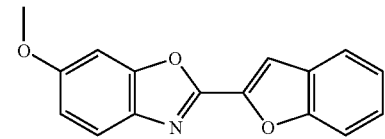
26-002

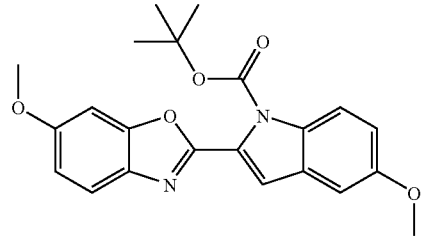
26-003

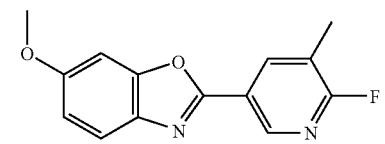
26-004

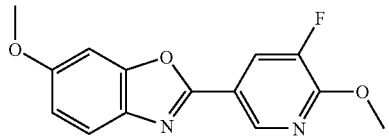
26-005

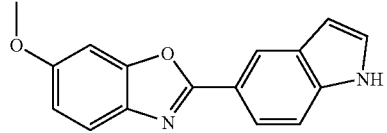
26-006

General procedure: 2-Bromo-6-methoxy-1,3-benzoxazole (0.263 mmol), Pd(dppf)Cl₂ (0.013 mmol), K₂CO₃ (aq.) and the corresponding arylboronic acid or ester (0.289 mmol) were stirred in DMF at 80° C. under argon for 1 h. The reaction mixture was allowed to cool to r.t. and brine was added. The reaction mixture was extracted with CH₂Cl₂ and the organic phase was filtered. The solvents were removed under reduced pressure and the residues purified by reverse phase HPLC to afford the title compounds. ¹H NMR (26-001, 400 MHz, Chloroform-d) δ ppm 8.99 (d, 1H) 8.34 (dd, 1H) 7.63 (d, 1H) 7.13 (d, 1H) 6.97 (dd, 1H) 6.88 (d, 1H) 4.04 (s, 3H) 3.90 (s, 3H); MS m/z 257 (M+H); ¹H NMR (26-002, 400 MHz, Chloroform-d) δ ppm 7.65 (d, 1H) 7.60 (d, 1H) 7.57 (dd, 1H) 7.53-7.48 (m, 1H) 7.37-7.42 (m, 2H) 7.09 (d, 1H) 6.95 (dd, 1H) 3.61 (s, 3H); MS m/z 266 (M+H); ¹H NMR (26-003, 400 MHz, Chloroform-d) δ ppm 8.14 (d, 1H) 7.68 (d, 1H) 7.15-7.05 (m, 4H) 7.03-6.97 (m, 1H) 3.90 (s, 3H) 3.88 (s, 3H) 1.37 (s, 9H); MS m/z 395 (M+H); ¹H NMR (26-004, 400 MHz, Chloroform-d) δ ppm 8.85 (s, 1H) 8.41 (d, 1H) 7.65 (d, 1H) 7.13 (d, 1H) 7.00 (dd, 1H) 3.90 (s, 3H) 2.40 (s, 3H); MS m/z 259 (M+H); ¹H NMR (26-005, 400 MHz, Chloroform-d) δ ppm 8.85 (s, 1H) 8.09 (dd, 1H) 7.63 (d, 1H) 7.12 (d, 1H) 6.98 (dd, 1H) 4.13 (s, 3H) 3.90 (s, 3H); MS m/z 275 (M+H); ¹H NMR (26-006, 400 MHz, Chloroform-d) δ ppm 8.55 (s, 1H) 8.36 (s br, 1H) 8.10 (dd, 1H) 7.64 (d, 1 H) 7.52 (dd, 1H) 7.31 (t, 1H) 7.14 (d, 1H) 6.96 (dd, 1H) 6.72-6.67 (m, 1 H) 3.91 (s, 3 H); MS m/z 265 (M+H).

Example 27

5-(6-Methoxy-1,3-benzoxazol-2-yl)-2-fluoropyridine

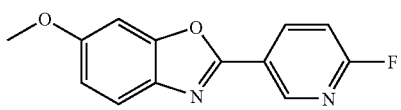

A solution of 2-hydroxy-4-methoxy-aniline hydrochloride (20.2 mmol) and triethylamine (2.9 mL) in dry MeOH (150 mL) was treated with 2-fluoro-5-formylpyridine (2.477 g).

The resulting mixture was stirred at rt for 40 mins and then concentrated to dryness to give 7.74 g of a reddish-orange solid. The residue was separated between CH₂Cl₂ (400 mL) and brine (200 mL) and the aqueous layer further extracted with (3×200 mL) CH₂Cl₂, the combined organics were then dried with Na₂SO₄, filtered and evaporated to give 5.36 g of an orange solid (quantitative yield): MS m/z 247 (M+H).

The residue was taken up in dry CH₂Cl₂ (250 mL) and 2,3-dichloro-5,6-dicyano-1,4-benzoquinone (DDQ, 5.59 g)

was added. After stirring at room temperature for 45 min, the resulting mixture was diluted with CH₂Cl₂ (500 mL), gravity filtered with a fluted filterpaper and the filtrate washed with saturated aqueous Na₂CO₃ (3×150 mL). The combined aqueous layers were back-extracted with (200 mL) CH₂Cl₂ and the combined organic layers washed with brine (200 mL). The organic layer was dried with Na₂SO₄ and evaporated to give 4.42 g of a brown solid. The crude was purified by flash column chromatography (SiO2, Heptane:EtOAc 0→100%) to give the title compound as a white solid 1.99 g (41% yield over two steps): 1H NMR δ ppm 8.98 (d, 1H) 8.61-8.69 (m, 1H) is 7.73 (d, 1H) 7.41-7.49 (m, 2H) 7.04 (dd, 1H) 3.86 (s, 3H); MS m/z 245 (M+H).

Example 28

Methyl 2-[2-(dimethylamino)pyrimidin-5-yl]-1,3-benzoxazole-6-carboxylate

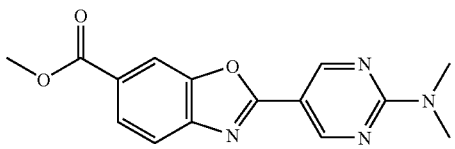

The synthesis was performed according to the procedure described for 5-(6-methoxy-1,3-benzoxazol-2-yl)-2-fluoropyridine starting with 180 mg of 2-dimethylamino-pyrimidine-5-carbaldehyde and 200 mg of methyl 4-amino-3-hydroxybenzoate to give 256.8 mg of the title compound.

1H NMR (400 MHz, chloroform-d) δ ppm 9.11 (s, 2H) 8.25 (d, 1H) 8.09 (dd, 1H) 7.73 (d, 1H) 3.97 (s, 3H) 3.33 (s, 6H); MS m/z 299 (M+H)

Example 29

2-{6-[(2-Fluoroethyl)amino]pyridin-3-yl}-1,3-benzoxazol-6-ol

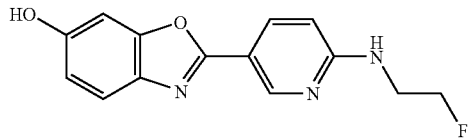

To N-(2-fluoroethyl)-5-(6-methoxy-1,3-benzoxazol-2-yl)pyridin-2-amine (0.18 mmol), in a microwave vial with a stir bar, was added tetrabutylammonium bromide (0.02 mmol) and hydrobromic acid 48%, w/w aq soln (5.0 mL). The reaction vessel was sealed and heated at 120° C. for 10 min. LCMS showed remaining starting material and the reaction was run an additional 10 min. The reaction mixture was neutralized with sat NaHCO₃ (100 mL), extracted with (3×50 mL) CH₂Cl₂, the combined organic layers were dried (Na₂SO₄) and evaporated to give 33.1 mg as a brown oil. Purified on prep HPLC to give 10.4 mg of the title compound as a tan solid after lyophilization. 1H NMR (400 MHz, Chloroform-d/MeOH-d₄ 1:1) δ ppm 8.75 (d, 1H) 8.05 (dd, 1H) 7.42 (d, 1H) 7.00 (d, 1H) 6.82 (dd, 1H) 6.63 (d, 1H) 4.62-4.66 (m, 1H) 4.50-4.54 (m, 1H) 3.71-3.76 (m, 1H) 3.64-3.69 (m, 1H); 19F (1H decoupled) NMR (400 MHz, Chloroform-d/MeOH-d₄) δ ppm −224.8; MS m/z 274 (M+H).

Precursors

The following examples are useful as precursors for the preparation of radiolabeled compounds of formula Ia.

Example a 2-(6-aminopyridin-3-yl)-1,3-benzoxazol-6-ol

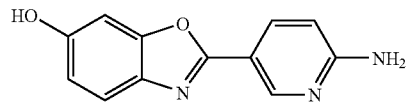

To a stirred and cooled (ice bath) solution of 5-(6-methoxy-1,3-benzoxazol-2-yl)pyridin-2-amine (2.07 mmol) in CH₂Cl₂ (50 mL) was slowly added boron tribromide 1M in CH₂Cl₂ (4.15 mL) from a pressure equalized dropping funnel. After full addition the reaction mixture was stirred 5 mins in the ice bath, before it was allowed to reach room temperature and then stirred at room temperature overnight. The reaction mixture was cooled (ice bath) and diluted with CH₂Cl₂ (100 mL), followed by EtOAc (100 mL), water (100 mL) and sat aq NaHCO₃ (100 mL) and the resulting mixture allowed to reach room temperature and stirred vigorously for 10 mins. The organic layer was separated and the aqueous layer extracted with CH₂Cl₂ (3×100 mL), the combined organic layers were dried (Na₂SO₄), filtered and evaporated to give 0.55 g of 2-(6-aminopyridin-3-yl)-1,3-benzoxazol-6-ol, as a pale yellow foamy solid. MS m/z 228 (M+H).

Example b 5-(6-{[tert-butyl(dimethyl)silyl]oxy}-1,3-benzoxazol-2-yl)pyridin-2-amine

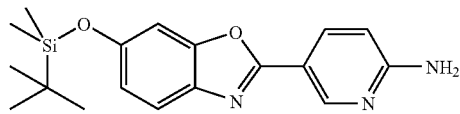

To a solution of 2-(6-aminopyridin-3-yl)-1,3-benzoxazol-6-ol (0.95 mmol) in DMF (25 mL) was added tert-butylchlorodimethylsilane (1.05 mmol) and imidazole (2.38 mmol), the resulting mixture was stirred at room temperature for 3 hours. LCMS showed no conversion. Additional tert-butylchlorodimethylsilane (1.05 mmol) and imidazole (2.38 mmol) was added to the reaction mixture, then stirred at room temperature overnight. The reaction mixture was then partitioned between EtOAc (100 mL) and water (250 mL), and the aqueous layer was extracted twice with EtOAc (100 mL). The combined organic layers were washed with brine (100 mL), dried (Na₂SO₄), filtered and evaporated to give 1.121 g of a yellow solid. Purified by flash column chromatography (SiO₂, Heptane:EtOAc 0→100%), to give the title compound (322.5 mg) as an ivory-white solid. ¹H NMR δ ppm 8.67 (d, 1H) 8.01 (dd, 1H) 7.54 (d, 1H) 7.18 (d, 1H) 6.85 (dd, 1H) 6.77 (s, 2H) 6.57 (d, 1H) 0.97 (s, 9H) 0.22 (s, 6H); MS m/z 342 (M+H).

BIOLOGICAL EXAMPLES

The following compounds are used as comparative compounds and are referred to in the text below by their indicated corresponding names:

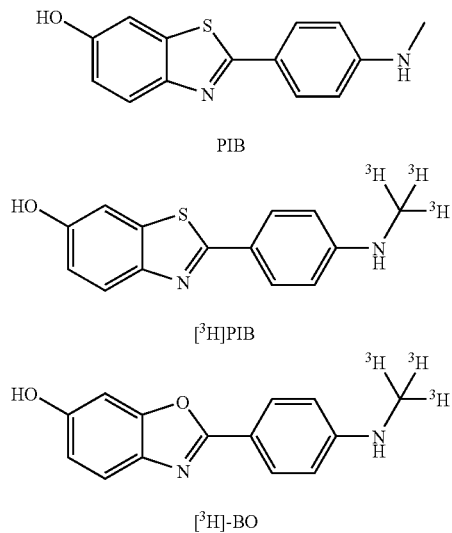

PIB

[³H]PIB

[³H]-BO

Compounds of the present invention can be or were tested in one or several of the following assays/experiments/studies:

Competition Binding Assay

Competition binding was performed in 384-well FB filter plates using synthetic Aβ 1-40 in 2.7 nM of [³H]PIB (or another ³H-labeled radioligand when so mentioned) in phosphate buffer at pH 7.5, by adding various concentrations of non-radioactive compounds originally dissolved in DMSO. The binding mixture was incubated for 30 min at room temperature, followed by vacuum filtration, and subsequentially by washing twice with 1% Triton-X100. Scintillation fluid was thereafter added to the collected Aβ 1-40 on the filter plate, and the activity of the bound remaining radioligand ([³H]PIB or another ³H-labeled radioligand) was measured using 1450 Microbeta from PerkinElmer (FIG. 1).

Saturation Binding Experiments

Saturation binding experiments were performed in 96-well polypropylene deep well plates. 2 μM human synthetic Aβ 1-40 fibrils in phosphate buffer pH 7.5, or buffer alone as control, were incubated with increasing concentration of a ³H-labeled radioligand of the present invention for 1 hr at room temperature. The radioactivity still bound to the Aβ 1-40 fibrils at the end of the incubation was detected on FB filters after filtration in a Brandel apparatus using a wash buffer containing 0.1% Triton-X100. Results were corrected for nonspecific, nondisplaceable binding defined as the number of counts from wells without Aβ 1-40 fibrils (replaced with assay buffer). The dissociation constant ($K_d$) and amount of binding sites (Bmax) were determined from the experimental results by non-linear regression analysis after demonstration of two site binding from Scatchard analysis (FIG. 2).

Dissociation Experiments

Dissociation experiments can be performed in 96-well polypropylene deep well plates. 2 μM human synthetic Aβ 1-40 fibrils in phosphate buffer pH 7.5, or buffer alone as control, is incubated with 9 nM of a ³H-labeled radioligand of the present invention for 4 h at room temperature. Dissociation is started at different time points, by the addition of an equal volume of a non-labeled compound of the present invention (10 μM) in 4% DMSO in phosphate buffer at pH 7.5. The radioactivity still bound to the Aβ 1-40 fibrils at the end of the incubation is detected on FB filters after filtration in a Brandel apparatus using a wash buffer containing 0.1% Triton-X100.

In Vivo Rat Brain Entry Studies

Brain exposure after i.v administration can be determined in rat brains using cassette dosing. Four different compounds are dosed followed by plasma and brain sampling at 2 and 30 minutes after the dosing. 2 to 30 min brain concentration ratios, and percentage of total of injected dose after 2 mins found in brain, are calculated. The compound concentrations are determined by analysis of protein precipitated plasma samples by reversed-phase liquid chromatography coupled to a electrospray tandem mass spectrometer.

Biological Example 1

Binding Parameters of a Compound of the Present Invention

Summation of binding parameters of a compound of the present invention: 2-[6-(methylamino)pyridin-3-yl]-1,3-benzooxazol-6-ol, at amyloid Aβ 1-40 fibrils in vitro is depicted in Table 1 below.

TABLE 1

Summation of binding parameters of a compound of the present invention: 2-[6-(methylamino)pyridin-3-yl]-1,3-benzooxazol-6-ol, at amyloid Aβ 1-40 fibrils in vitro.

|  | AVG | SEM |
| --- | --- | --- |
| IC50 (nM) | 182.5 | 2.507 |
| Kd 1 (nM) | 5.3255 | 1.986 |
| Kd 2 (nM) | 63.3 | 0.893 |
| Bmax 1 (pmol/nmol Ab) | 0.90985 | 0.262 |
| Bmax 2 (pmol/nmol Ab) | 4.298 | 0.119 |

Biological Example 2

Characterization of Specific Binding of Novel Heteroaryl Substituted Benzoxazole Derivatives to Aβ Amyloid Fibrils In Vitro.

Specific binding was determined according to the competion binding assay described herein. The determined $IC_{50}$'s in the competion binding assays (using [³H]PIB as radioligand) of 5 compounds of the present invention are shown in Table 2.

TABLE 2

$IC_{50}$'s of 5 exemplified compounds of the present invention when run in the competion binding assay.

| NAME | EXAMPLE | IC50 (nM) |
| --- | --- | --- |
| 5-(6-Methoxy-1,3-benzoxazol-2-yl)-N,N-dimethylpyridin-2-amine | 1 | 204 |

TABLE 2-continued

IC$_{50}$'s of 5 exemplified compounds of the present invention when run in the competion binding assay.

| NAME | EXAMPLE | IC50 (nM) |
|---|---|---|
| 2-[6-(Dimethylamino)pyridin-3-yl]-1,3-benzoxazol-6-ol | 2 | 85 |
| 5-(6-Methoxy-1,3-benzoxazol-2-yl)-N-methylpyridin-2-amine | 3 | 186 |
| N-[5-(6-Methoxy-1,3-benzoxazol-2-yl)pyridin-2-yl]-N-methylacetamide | 4 | 15655 |
| 2-[6-(Methylamino)pyridin-3-yl]-1,3-benzoxazol-6-ol | 5 | 182 |

Binding to Amyloid Plaques in Post-Mortem Human AD Brains

Human cortical sections (7 μm) from AD patient(s) and control subject(s) were obtained from a Dutch tissue bank. Sections were incubated for 30 minutes at room temperature in 50 mM Tris HCl (pH 7.4) buffer containing tritium-labeled compound (1 nM). Incubation was terminated by 3 consecutive 10-minute rinses in buffer (1° C.) followed by a rapid rinse in distilled water (1° C.). Sections were air dried in front of a fan. Dried sections and plastic tritium standards (Amersham microscales-$^3$H) were apposed to phosphoimage plates (Fuji) in a cassette and exposed overnight. The following morning, the image plates were processed with a Fuji phospoimager (BAS 2500) using BAS Reader software. The resulting image was converted to TIF format using Aida software, optimized with Adobe Photoshop (v 8.0) and quantified using Image-J (NIH). Data were statistically analyzed using Excel (FIGS. 3-5).

Binding in Transgenic (APP/PS1) Mouse Brain After Compound Administration In-Vivo Naïve, awake mice were restrained and intravenously infused with a tritium labeled compound of the present invention via the tail vein. The animals were rapidly anesthetized with isofluorane and decapitated 10 minutes after compound administration (1 mCi). Brains were removed and frozen with powdered dry ice. Brains were sectioned (10 μm) with a cryostat, thaw-mounted onto superfrost microscope slides and air-dried. Methods designed to optimize the imaging of bound ligand after in vivo administration were thereafter employed. To selectively reduce unbound radioactivity levels, one-half of the sections were rinsed (3×10 minutes) in cold (1° C.) Tris buffer (50 mM, pH7.4) followed by a rapid rinse in cold (1° C.) deionized water. Sections were then air dried in is front of a fan. Rinsed as well as unrinsed sections and tritium standards were exposed to phosphoimage plates (Fuji). Phosphoimage plates were processed with a Fujifilm BAS-2500 phosphoimager using BAS Reader software (FIG. 6).

The invention claimed is:

1. A compound or a pharmaceutically acceptable salt thereof, wherein:
the compound corresponds to Formula Ia:

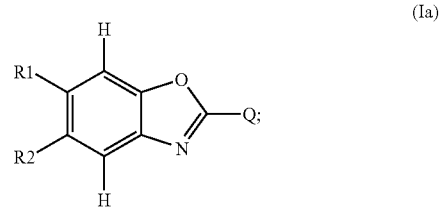

(Ia)

R1 is selected from the group consisting of hydrogen, halo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoro alkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N ($C_{1-3}$ alkyl)$C_{1-3}$ fluoroalkyl, (CO)N($C_{4-6}$ alkylene), (CO)N($C_{4-6}$ fluoroalkylene), nitro, and cyano;

R2 is selected from the group consisting of hydrogen, fluoro, bromo, iodo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN ($C_{1-3}$ alkyl)$C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2$$C_{1-3}$ alkyl, NHSO$_2$$C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO) NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO) N($C_{4-6}$ alkylene), (CO)N($C_{4-6}$ fluoroalkylene), and cyano;

Q is a pyrimidine ring:

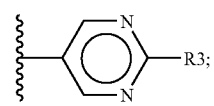

R3 is selected from the group consisting of fluoro, bromo, iodo, $C_{1-4}$ alkyl, $C_{1-4}$ fluoroalkyl, $C_{1-3}$ alkyleneO$C_{1-3}$ alkyl, $C_{1-3}$ alkyleneO$C_{1-3}$ fluoroalkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$$C_{1-3}$ alkyleneN($C_{1-3}$ alkyl)$C_{1-3}$ fluoroalkyl, hydroxy, $C_{1-4}$ alkoxy, $C_{1-4}$ fluoroalkoxy, amino, NH$C_{1-3}$ alkyl, NH$C_{1-3}$ fluoroalkyl, N($C_{1-3}$ alkyl)$_2$, N(C$_{1-3}$ fluoroalkyl)$_2$, N(C$_{1-3}$ alkyl)C$_{1-3}$ fluoroalkyl, NH(CO$_3$ alkylene)G2, N(C$_{0-1}$ alkyl)N(C$_{0-1}$ alkyl)$_2$, N(C$_{0-1}$ alkyl)OC$_{0-1}$ alkyl, NC$_{1-3}$ alkyl(CO)C$_{1-3}$ alkyl, NH(CO)C$_{1-3}$ alkyl, NH(CO)C$_{1-3}$ fluoroalkyl, NH(CO)G2, (CO)C$_{1-3}$ alkyl, (CO)C$_{1-3}$ fluorolkyl, (CO) C$_{1-3}$ alkoxy, (CO)C$_{1-3}$ fluoroalkoxy, (CO)NH$_2$, (CO) NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl) C$_{1-3}$ fluoroalkyl, (CO)N(C$_{4-6}$ alkylene), (CO)N(C$_{4-6}$ fluoroalkylene), (CO)G2, (CO)NH$_2$G2, SC$_{1-3}$ alkyl, SC$_{1-3}$ fluoroalkyl, SO$_2$NH$_2$, SO$_2$NHC$_{1-3}$ alkyl, SO$_2$NHC$_{1-3}$ fluoroalkyl, SO$_2$N(C$_{1-3}$ alkyl)$_2$, SO$_2$N(C$_{1-3}$ fluoroalkyl)$_2$, SO$_2$N(C$_{1-3}$ alkyl)C$_{1-3}$ fluoroalkyl, cyano, and G1;

G1 is:

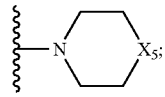

X$_5$ is selected from the group consisting of O, NH, NC$_{1-3}$ alkyl, and NC$_{1-3}$ fluoroalkyl;

G2 is phenyl optionally substituted with a substituent selected from the group consisting of fluoro, bromo, iodo, methyl, and methoxy; and one or more of the atoms of formula Ia is/are optionally a detectable isotope;

with the following provisos:
when R1 and R2 both are H, R3 is not NH(C$_{0-1}$ alkylene) G2, G1, chloro, hydroxy, SCH$_3$, NHC$_{0-1}$ alkyl, N(C$_{1-2}$ alkyl)$_2$, NHNH$_2$, or NHOH;
when R3 is amino, R1 or R2 is not methyl, ethyl, chloro, or bromo; and
the compound is not:
5-(6-methyl-1,3-benzoxazol-2-yl)pyrimidin-2-amine, or
5-(6-methoxy-1,3-benzoxazol-2-yl)-N-phenylpyrimidin-2-amine.

2. A compound or pharmaceutically acceptable salt thereof, wherein:
the compound corresponds to Formula Ia:

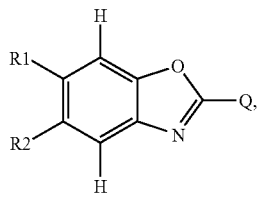

Q is Q4:

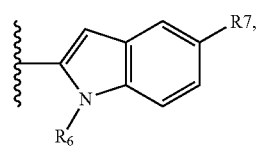

R1 is methoxy,
R2 is hydrogen,

R6 is (CO)C$_{1-4}$ alkoxy,
R7 is C$_{1-4}$ alkoxy, and
one or more of the atoms of formula Ia is/are optionally a detectable isotope.

3. A compound or a pharmaceutically acceptable salt thereof, wherein:
the compound corresponds to Formula Ia:

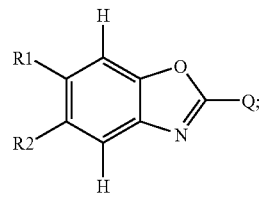

Q is Q2:

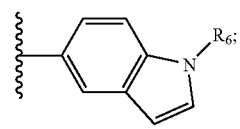

R1 is methoxy;
R2 is hydrogen;
R6 is selected from the group consisting of hydrogen, C$_{1-4}$ alkyl, C$_{1-4}$ fluoroalkyl, and (CO)C$_{1-4}$ alkoxy; and
one or more of the atoms of formula Ia is/are optionally a detectable isotope.

4. A compound or a pharmaceutically acceptable salt thereof, wherein:
the compound corresponds to formula Ia:

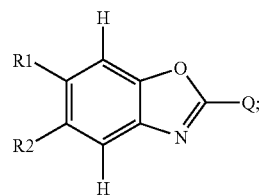

one atom of formula Ia is $^{11}$C, $^{18}$F, $^{123}$I, or $^{125}$I;
one of R1 and R2 is hydroxy, iodo, $^{123}$I, $^{125}$I, or [$^{11}$C] methoxy;
one of R1 and R2 is H;
Q is Q1:

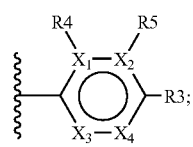

Q1 is a 6-membered aromatic heterocycle containing one or two N atoms;

R3 is selected from the group consisting of NHCH$_3$, N(CH$_3$)$_2$, NH$^{11}$CH$_3$, N(CH$_3$)$^{11}$CH$_3$, NHCH$_2$CH$_2$ $^{18}$F, and OCH$_2$CH$_2$ $^{18}$F;

X$_2$ and X$_4$ are independently selected from the group consisting of N and C;

X$_1$ and X$_3$ are C;

the C of X$_1$ is optionally substituted with R4;

when X$_2$ is C, the C is optionally substituted with R5;

R4 is selected from the group consisting of fluoro, bromo, iodo, C$_{1-4}$ alkyl, C$_{1-4}$ fluoroalkyl, C$_{1-4}$ alkoxy, C$_{1-4}$ fluoroalkoxy, amino, NHC$_{1-3}$ alkyl, and NHC$_{1-3}$ fluoroalkyl; and R5 is selected from the group consisting of fluoro, bromo, iodo, C$_{1-4}$ alkyl, C$_{1-4}$ fluoroalkyl, C$_{1-4}$ alkoxy, C$_{1-4}$ fluoroalkoxy, amino, NHC$_{1-3}$ alkyl, and NHC$_{1-3}$ fluoroalkyl.

5. A compound or a pharmaceutically acceptable salt thereof, wherein:

the compound corresponds to formula I:

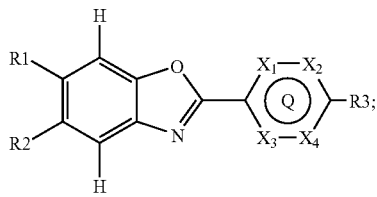

(I)

one atom of formula I is $^{11}$C, $^{123}$I, or $^{125}$I;

one of R1 and R2 is hydroxy, iodo, $^{123}$I, $^{125}$I, or [$^{11}$C] methoxy;

one of R1 and R2 is H;

R3 is selected from the group consisting of NHCH$_3$, N(CH$_3$)$_2$, NH$^{11}$CH$_3$, and N(CH$_3$)$^{11}$CH$_3$;

Q is a pyridine ring, wherein one of X$_3$ and X$_4$ is N, and the remaining of X$_1$, X$_2$, X$_3$, and X$_4$ are C; and each C of X$_1$, X$_2$, X$_3$, and X$_4$ has a hydrogen substituent.

6. A compound or a pharmaceutically acceptable salt thereof, wherein:

the compound corresponds to Formula Ia:

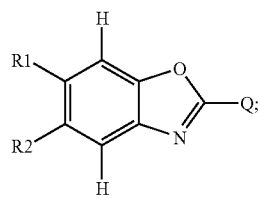

(Ia)

R1 is selected from the group consisting of hydrogen, halo, C$_{1-6}$ alkyl, C$_{1-6}$ fluoroalkyl, C$_{1-3}$ alkyleneOC$_{1-3}$ alkyl, C$_{1-3}$ alkyleneOC$_{1-3}$ fluorolkyl, C$_{1-3}$ alkyleneNH$_2$, C$_{1-3}$ alkyleneNHC$_{1-3}$ alkyl, C$_{1-3}$ alkyleneN(C$_{1-3}$ alkyl)$_2$, C$_{1-3}$ alkyleneNHC$_{1-3}$ fluoroalkyl, C$_{1-3}$ alkyleneN(C$_{1-3}$ fluoroalkyl)$_2$, C$_{1-3}$ alkyleneN(C$_{1-3}$ alkyl)C$_{1-3}$ fluoroalkyl, hydroxy, C$_{1-6}$ alkoxy, C$_{1-6}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(CO)C$_{1-3}$ alkyl, NH(CO)C$_{1-3}$ fluoroalkyl, NH(CO)C$_{1-3}$ alkoxy, NH(CO)C$_{1-3}$ fluoroalkoxy, NHSO$_2$C$_{1-3}$ alkyl, NHSO$_2$C$_{1-3}$ fluoroalkyl, (CO)C$_{1-3}$ alkyl, (CO)C$_{1-3}$ fluoroalkyl, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene), nitro, and cyano;

R2 is selected from the group consisting of hydrogen, fluoro, bromo, iodo, C$_{1-6}$ alkyl, C$_{1-6}$ fluoroalkyl, C$_{1-3}$ alkyleneOC$_{1-3}$ alkyl, C$_{1-3}$ alkyleneOC$_{1-3}$ fluorolkyl, C$_{1-3}$ alkyleneNH$_2$, C$_{1-3}$ alkyleneNHC$_{1-3}$ alkyl, C$_{1-3}$ alkyleneN(C$_{1-3}$ alkyl)$_2$, C$_{1-3}$ alkyleneNHC$_{1-3}$ fluoroalkyl, C$_{1-3}$ alkyleneN(C$_{1-3}$ fluoroalkyl)$_2$, C$_{1-3}$ alkyleneN(C$_{1-3}$ alkyl)C$_{1-3}$ fluoroalkyl, hydroxy, C$_{1-6}$ alkoxy, C$_{1-6}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(CO)C$_{1-3}$ alkyl, NH(CO)C$_{1-3}$ fluoroalkyl, NH(CO)C$_{1-3}$ alkoxy, NH(CO)C$_{1-3}$ fluoroalkoxy, NHSO$_2$C$_{1-3}$ alkyl, NHSO$_2$C$_{1-3}$ fluoroalkyl, (CO)C$_{1-3}$ alkyl, (CO)C$_{1-3}$ fluoroalkyl, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene), and cyano;

Q is a nitrogen-containing aromatic heterocycle selected from the group consisting of:

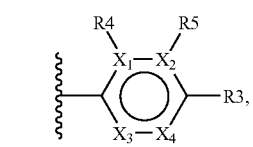

Q1

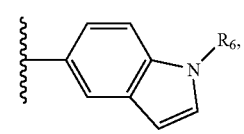

Q2

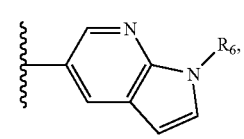

Q3

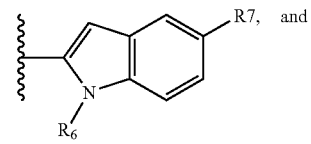

Q4

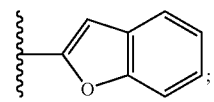

Q5

Q1 is a 6-membered aromatic heterocycle containing one or two N atoms;

X$_1$, X$_2$, X$_3$, and X$_4$ are independently selected from the group consisting of N and C, wherein:

one or two of X$_1$, X$_2$, X$_3$, and X$_4$ is/are N and the remaining are C, and when X$_1$ is C, the C is optionally substituted with R4, and when X$_2$ is C, the C is optionally substituted with R5;

R3 is selected from the group consisting of fluoro, bromo, iodo, C$_{1-4}$ alkyl, C$_{1-4}$ fluoroalkyl, C$_{1-3}$ alkyleneOC$_{1-3}$ alkyl, C$_{1-3}$ alkyleneOC$_{1-3}$ fluoroalkyl, C$_{1-3}$ alkyleneNH$_2$, C$_{1-3}$ alkyleneNHC$_{1-3}$ alkyl, C$_{1-3}$ alkyleneN(C$_{1-3}$ alkyl)$_2$, C$_{1-3}$ alkyleneNHC$_{1-3}$ fluoroalkyl, C$_{1-3}$ alkyleneN(C$_{1-3}$ fluoroalkyl)$_2$, C$_{1-3}$ alkyleneN(C$_{1-3}$ alkyl)C$_{1-3}$ fluoroalkyl, hydroxy, C$_{1-4}$ alkoxy, C$_{1-4}$ fluoroalkoxy, amino, NHC$_{1-3}$ alkyl, NHC$_{1-3}$ fluoroalkyl, N(C$_{1-3}$ alkyl)$_2$, N(C$_{1-3}$ fluoroalkyl)$_2$, N(C$_{1-3}$ alkyl)C$_{1-3}$ fluoroalkyl, NH(CO$_3$ alkylene)G2, N(C$_{0-1}$ alkyl)N(C$_{0-1}$ alkyl), N(C$_{0-1}$ alkyl)OC$_{0-1}$ alkyl, NC$_{1-3}$ alkyl(CO)C$_{1-3}$ alkyl, NH(CO)C$_{1-3}$ alkyl, NH(CO)C$_{1-3}$ fluoroalkyl, NH(CO)G2, (CO)C$_{1-3}$ alkyl, (CO)C$_{1-3}$ fluorolkyl, (CO)C$_{1-3}$ alkoxy, (CO)C$_{1-3}$ fluoroalkoxy, (CO)NH$_2$, (CO)NHC$_{1-3}$ alkyl, (CO)NHC$_{1-3}$ fluoroalkyl, (CO)N(C$_{1-3}$ alkyl)$_2$, (CO)N(C$_{1-3}$ fluoroalkyl)$_2$, (CO)N(C$_{1-3}$ alkyl)C$_{1-3}$ fluoroalkyl, (CO)N(C$_{4-6}$ alkylene), (CO)N(C$_{4-6}$ fluoroalkylene), (CO)G2, (CO)NH$_2$G2, SC$_{1-3}$ alkyl, SC$_{1-3}$ fluoroalkyl, SO$_2$NH, SO$_2$NHC$_{1-3}$ alkyl, SO$_2$NHC$_{1-3}$ fluoroalkyl, SO$_2$N(C$_{1-3}$ alkyl)$_2$, SO$_2$N(C$_{1-3}$ fluoroalkyl)$_2$, SO$_2$N(C$_{1-3}$ alkyl)C$_{1-3}$ fluoroalkyl, cyano, and G1;

G1 is:

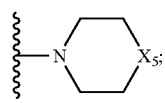

$X_5$ is selected from the group consisting of O, NH, NC$_{1-3}$ alkyl, and NC$_{1-3}$ fluoroalkyl;

G2 is phenyl optionally substituted with a substituent selected from the group consisting of fluoro, bromo, iodo, methyl, and methoxy;

at least one of the atoms of R1, R2, or R3 is a radiolabeled atom;

R4 is selected from the group consisting of fluoro, bromo, iodo, C$_{1-4}$ alkyl, C$_{1-4}$ fluoroalkyl, C$_{1-4}$ alkoxy, C$_{1-4}$ fluoroalkoxy, amino, NHC$_{1-3}$ alkyl, and NHC$_{1-3}$ fluoroalkyl;

R5 is selected from the group consisting of fluoro, bromo, iodo, C$_{1-4}$ alkyl, C$_{1-4}$ fluoroalkyl, C$_{1-4}$ alkoxy, C$_{1-4}$ fluoroalkoxy, amino, NHC$_{1-3}$ alkyl, and NHC$_{1-3}$ fluoroalkyl;

R6 is selected from the group consisting of hydrogen, C$_{1-4}$ alkyl, C$_{1-4}$ fluoroalkyl, and (CO)C$_{1-4}$ alkoxy; and R7 is selected from the group consisting of hydrogen, fluoro, bromo, iodo, C$_{1-4}$ alkoxy, and C$_{1-4}$ fluoroalkoxy;

with the following provisos:
when R1 and R2 both are H, and X$_2$ and X$_4$ are N, R3 is not NH(C$_{0-1}$ alkylene)G2, G1, chloro, hydroxy, SCH$_3$, NHC$_{0-1}$ alkyl, N(C$_{1-2}$ alkyl)$_2$, NHNH$_2$, or NHOH;

when R1 and R2 both are H, and either of X$_2$ and X$_4$ is N while the other is C, R3 is not chloro, hydroxy, or methyl;

when Q is Q5 and R2 is hydrogen, R1 is not hydrogen or halo;

when Q is Q5 and R2 is C$_{1-6}$ alkyl, R1 is not hydrogen;

when R3 is amino and X$_2$ and X$_4$ both are N, R1 or R2 is not methyl, ethyl, chloro, or bromo; and the compound is not:
2-(5-aminopyridin-2-yl)-1,3-benzoxazol-6-amine,
5-(6-methyl-1,3-benzoxazol-2-yl)pyrimidin-2-amine,
5-(6-methoxy-1,3-benzoxazol-2-yl)-N-phenylpyrimidin-2-amine,
2-(5-methylpyridin-2-yl)-1,3-benzoxazole, or
5-methyl-2-(6-methylpyridin-3-yl)-1,3-benzoxazole.

7. A compound or salt thereof according to claim 6, wherein at least one of the atoms of R2 is a radiolabeled atom.

8. A compound or salt thereof according to claim 6, wherein at least one of the atoms of R3 is a radiolabeled atom.

9. A compound or salt thereof according to claim 6, wherein at least one of the atoms of R1 is a radiolabeled atom.

10. A compound or salt thereof according to claim 9, wherein:
the compound corresponds to formula I:

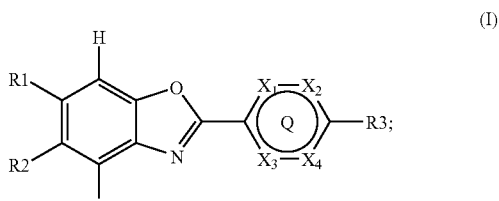

Q is a 6-membered aromatic heterocycle containing either one or two N-atoms; and $X_1, X_2, X_3$, and $X_4$ are independently selected from N or C, wherein:
one or two of $X_1, X_2, X_3$, and $X_4$ is N, and the remaining are C; and
each C of $X_1, X_2, X_3$, and $X_4$ has a hydrogen substituent.

11. A compound or salt thereof according to claim 7, wherein:
the compound corresponds to formula I:

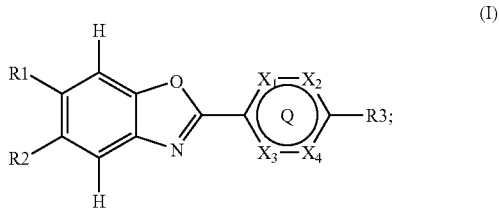

Q is a 6-membered aromatic heterocycle containing either one or two N-atoms; and $X_1, X_2, X_3$, and $X_4$ are independently selected from N or C, wherein:
one or two of $X_1, X_2, X_3$, and $X_4$ is N, and the remaining are C; and
each C of $X_1, X_2, X_3$, and $X_4$ has a hydrogen substituent.

12. A compound or salt thereof according to claim 8, wherein:
the compound corresponds to formula I:

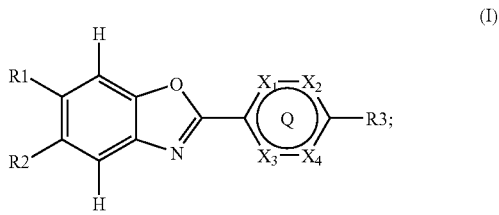

Q is a 6-membered aromatic heterocycle containing either one or two N-atoms; and $X_1, X_2, X_3$, and $X_4$ are independently selected from N or C, wherein:
one or two of $X_1, X_2, X_3$, and $X_4$ is N, and the remaining are C; and
each C of $X_1, X_2, X_3$, and $X_4$ has a hydrogen substituent.

13. A compound or a pharmaceutically acceptable salt thereof, wherein:

the compound corresponds to Formula Ia:

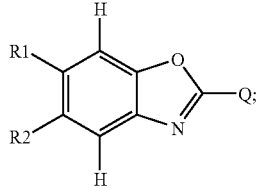

(Ia)

R1 is selected from the group consisting of hydrogen, halo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-6}$ alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2C_{1-3}$ alkyl, NHSO$_2C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), nitro, and cyano;

R2 is selected from the group consisting of hydrogen, fluoro, bromo, iodo, $C_{1-6}$ alkyl, $C_{1-6}$ fluoroalkyl, $C_{1-3}$ alkyleneO$C_{1-3}$ alkyl, $C_{1-3}$ alkyleneO$C_{1-3}$ fluorolkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, alkoxy, $C_{1-6}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO)$C_{1-3}$ alkyl, NH(CO)$C_{1-3}$ fluoroalkyl, NH(CO)$C_{1-3}$ alkoxy, NH(CO)$C_{1-3}$ fluoroalkoxy, NHSO$_2C_{1-3}$ alkyl, NHSO$_2C_{1-3}$ fluoroalkyl, (CO)$C_{1-3}$ alkyl, (CO)$C_{1-3}$ fluoroalkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), and cyano;

Q is a nitrogen-containing aromatic heterocycle selected from the group consisting of:

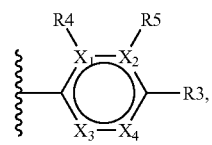

Q1

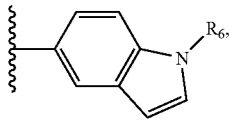

Q2

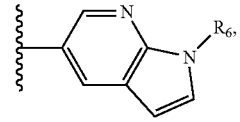

Q3

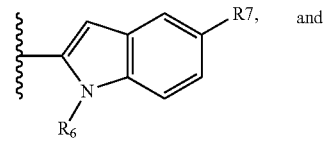

Q4 and

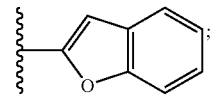

Q5

Q1 is a 6-membered aromatic heterocycle containing one or two N atoms;

$X_1$, $X_2$, $X_3$, and $X_4$ are independently selected from the group consisting of N and C, wherein:
one or two of $X_1$, $X_2$, $X_3$, and $X_4$ is/are N and the remaining are C, and
when $X_1$ is C, the C is optionally substituted with R4, and
when $X_2$ is C, the C is optionally substituted with R5;

R3 is selected from the group consisting of fluoro, bromo, iodo, $C_{1-4}$ alkyl, $C_{1-4}$ fluoroalkyl, $C_{1-3}$ alkyleneO$C_{1-3}$ alkyl, $C_{1-3}$ alkyleneO$C_{1-3}$ fluoroalkyl, $C_{1-3}$ alkyleneNH$_2$, $C_{1-3}$ alkyleneNH$C_{1-3}$ alkyl, $C_{1-3}$ alkyleneN($C_{1-3}$ alkyl)$_2$, $C_{1-3}$ alkyleneNH$C_{1-3}$ fluoroalkyl, $C_{1-3}$ alkyleneN($C_{1-3}$ fluoroalkyl)$_2$, $C_{1-3}$ alkyleneN($C_{1-3}$ alkyl)$C_{1-3}$ fluoroalkyl, hydroxy, $C_{1-4}$ alkoxy, $C_{1-4}$ fluoroalkoxy, amino, NH$C_{1-3}$ alkyl, NH$C_{1-3}$ fluoroalkyl, N($C_{1-3}$ alkyl)$_2$, N($C_{1-3}$ fluoroalkyl)$_2$, N($C_{1-3}$ alkyl)$C_{1-3}$ fluoroalkyl, NH(CO$_3$ alkylene)G2, N($C_{0-1}$ alkyl)N($C_{0-1}$ alkyl), N($C_{0-1}$ alkyl)O$C_{0-1}$ alkyl, N$C_{1-3}$ alkyl(CO)$C_{1-3}$ alkyl, NH(CO)$C_{1-3}$ alkyl, NH(CO)$C_{1-3}$ fluoroalkyl, NH(CO)G2, (CO)$C_{1-3}$ alkyl, (CO)$C_{1-3}$ fluorolkyl, (CO)$C_{1-3}$ alkoxy, (CO)$C_{1-3}$ fluoroalkoxy, (CO)NH$_2$, (CO)NH$C_{1-3}$ alkyl, (CO)NH$C_{1-3}$ fluoroalkyl, (CO)N($C_{1-3}$ alkyl)$_2$, (CO)N($C_{1-3}$ fluoroalkyl)$_2$, (CO)N($C_{1-3}$ alkyl)$C_{1-3}$ fluoroalkyl, (CO)N($C_{4-6}$ alkylene), (CO)N($C_{4-6}$ fluoroalkylene), (CO)G2, (CO)NH$_2$G2, S$C_{1-3}$ alkyl, S$C_{1-3}$ fluoroalkyl, SO$_2$NH$_2$, SO$_2$NH$C_{1-3}$ alkyl, SO$_2$NH$C_{1-3}$ fluoroalkyl, SO$_2$N($C_{1-3}$ alkyl)$_2$, SO$_2$N($C_{1-3}$ fluoroalkyl)$_2$, SO$_2$N($C_{1-3}$ alkyl)$C_{1-3}$ fluoroalkyl, cyano, and G1;

G1 is:

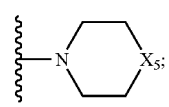

G1

$X_5$ is selected from the group consisting of O, NH, N$C_{1-3}$ alkyl, and N$C_{1-3}$ fluoroalkyl;

G2 is phenyl optionally substituted with a substituent selected from the group consisting of fluoro, bromo, iodo, methyl, and methoxy;

R4 is selected from the group consisting of fluoro, bromo, iodo, $C_{1-4}$ alkyl, $C_{1-4}$ fluoroalkyl, $C_{1-4}$ alkoxy, $C_{1-4}$ fluoroalkoxy, amino, NH$C_{1-3}$ alkyl, and NH$C_{1-3}$ fluoroalkyl;

R5 is selected from the group consisting of fluoro bromo iodo $C_{1-4}$ alkyl, $C_{1-4}$ fluoroalkyl, $C_{1-4}$ alkoxy, $C_{1-4}$ fluoroalkoxy, amino, $NHC_{1-3}$ alkyl, and $NHC_{1-3}$ fluoroalkyl;

R6 is selected from the group consisting of hydrogen, $C_{1-4}$ alkyl, $C_{1-4}$ fluoroalkyl, and $(CO)C_{1-4}$ alkoxy;

R7 is selected from the group consisting of hydrogen, fluoro, bromo, iodo, $C_{1-4}$ alkoxy, and $C_{1-4}$ fluoroalkoxy; and at least one of the atoms of formula Ia is a radiolabeled atom selected from the group consisting of $^{3}H$, $^{18}F$, $^{19}F$, $^{11}C$, $^{13}C$, $^{14}C$, $^{75}Br$, $^{76}Br$, $^{120}I$, $^{123}I$, $^{125}I$, and $^{131}I$;

with the following provisos:

when R1 and R2 both are H, and $X_2$ and $X_4$ both are N, R3 is not $NH(C_{0-1}$ alkylene)G2, G1, chloro, hydroxy, $SCH_3$, $NHC_{0-1}$ alkyl, $N(C_{1-2}$ alkyl)$_2$, $NHNH_2$, or NHOH;

when R1 and R2 both are H, and either of $X_2$ and $X_4$ is N while the other is C, R3 is not chloro, hydroxy, or methyl;

when Q is Q5 and R2 is hydrogen, R1 is not hydrogen or halo;

when Q is Q5 and R2 is $C_{1-6}$ alkyl, R1 is not hydrogen;

when R3 is amino and $X_2$ and $X_4$ both are N, R1 or R2 is not methyl, ethyl, chloro, or bromo; and the compound is not:
2-(5-aminopyridin-2-yl)-1,3-benzoxazol-6-amine,
5-(6-methyl-1,3-benzoxazol-2-yl)pyrimidin-2-amine,
5-(6-methoxy-1,3-benzoxazol-2-yl)-N-phenylpyrimidin-2-amine,
2-(5-methylpyridin-2-yl)-1,3-benzoxazole, or
5-methyl-2-(6-methylpyridin-3-yl)-1,3-benzoxazole.

14. A compound according to claim 8, wherein said radiolabeled atom is selected from the group consisting of $^{3}H$, $^{18}F$, $^{19}F$, $^{11}C$, $^{14}C$, and $^{123}I$.

15. A compound according to claim 13, wherein said radiolabeled atom is selected from the group consisting of $^{123}I$, $^{18}F$, and $^{11}C$.

16. A compound according to claim 13, wherein said radiolabeled atom is $^{11}C$.

17. A compound according to claim 13, wherein said radiolabeled atom is $^{18}F$.

18. A compound according to claim 13, wherein said radiolabeled atom is $^{123}I$.

19. A compound or salt thereof according to claim 13, wherein:

the compound corresponds to formula I:

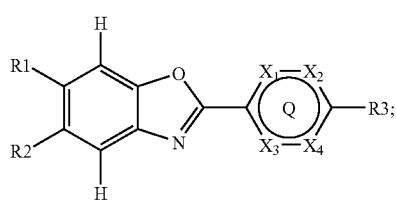

Q is a 6-membered aromatic heterocycle containing either one or two N-atoms; and $X_1$, $X_2$, $X_3$, and $X_4$ are independently selected from N or C, wherein:

one or two of $X_1$, $X_2$, $X_3$, and $X_4$ is N, and the remaining are C; and each C of $X_1$, $X_2$, $X_3$, and $X_4$ has a hydrogen substituent.

20. A compound or salt thereof according to claim 14, wherein:

the compound corresponds to formula I:

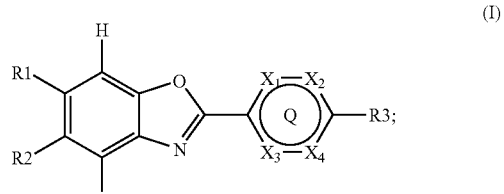

Q is a 6-membered aromatic heterocycle containing either one or two N-atoms; and $X_1$, $X_2$, $X_3$, and $X_4$ are independently selected from N or C, wherein:

one or two of $X_1$, $X_2$, $X_3$, and $X_4$ is N, and the remaining are C; and each C of $X_1$, $X_2$, $X_3$, and $X_4$ has a hydrogen substituent.

21. A compound or salt thereof according to claim 15, wherein:

the compound corresponds to formula I:

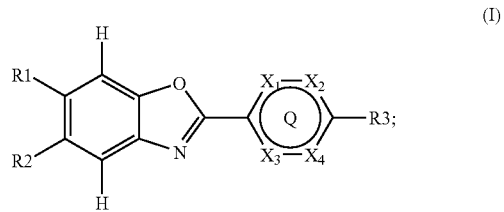

Q is a 6-membered aromatic heterocycle containing either one or two N-atoms; and $X_1$, $X_2$, $X_3$, and $X_4$ are independently selected from N or C, wherein:

one or two of $X_1$, $X_2$, $X_3$, and $X_4$ is N, and the remaining are C; and each C of $X_1$, $X_2$, $X_3$, and $X_4$ has a hydrogen substituent.

22. A compound or salt thereof according to claim 16, wherein:

the compound corresponds to formula I:

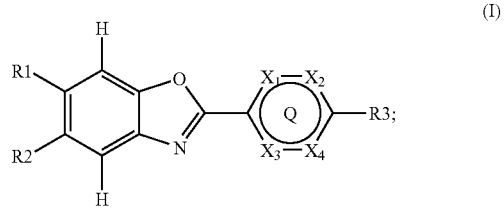

Q is a 6-membered aromatic heterocycle containing either one or two N-atoms; and $X_1$, $X_2$, $X_3$, and $X_4$ are independently selected from N or C, wherein:

one or two of $X_1$, $X_2$, $X_3$, and $X_4$ is N, and the remaining are C; and each C of $X_1$, $X_2$, $X_3$, and $X_4$ has a hydrogen substituent.

23. A compound or salt thereof according to claim 17, wherein:

the compound corresponds to formula I:

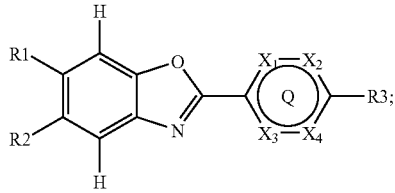

(I)

Q is a 6-membered aromatic heterocycle containing either one or two N-atoms; and $X_1, X_2, X_3$, and $X_4$ are independently selected from N or C, wherein:

one or two of $X_1, X_2, X_3$, and $X_4$ is N, and the remaining are C; and each C of $X_1, X_2, X_3$, and $X_4$ has a hydrogen substituent.

24. A compound or salt thereof according to claim 18, wherein:

the compound corresponds to formula I:

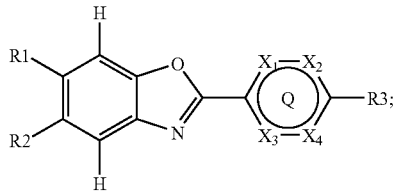

(I)

Q is a 6-membered aromatic heterocycle containing either one or two N-atoms; and $X_1, X_2, X_3$, and $X_4$ are independently selected from N or C, wherein:

one or two of $X_1, X_2, X_3$, and $X_4$ is N, and the remaining are C; and each C of $X_1, X_2, X_3$, and $X_4$ has a hydrogen substituent.

25. A compound or pharmaceutically acceptable salt thereof, wherein:

the compound is:

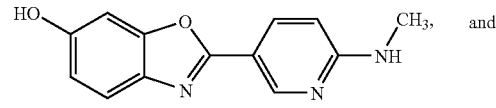 and one or more of the atoms in the compound or salt is/are optionally a detectable isotope.

26. A compound or pharmaceutically acceptable salt thereof, wherein the compound is:

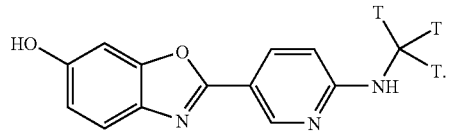

27. A pharmaceutical composition, wherein the pharmaceutical composition comprises:

a compound or salt thereof according to claim 25, and a pharmaceutically acceptable carrier.

28. A pharmaceutical composition, wherein:

the composition is useful for in vivo imaging of amyloid deposits; and the pharmaceutical composition comprises:

a compound or salt thereof according to claim 25, and a pharmaceutically acceptable carrier.

29. An in vivo method for measuring amyloid deposits in a subject, wherein the method comprises:

administering a detectable quantity of a pharmaceutical composition according to claim 27, and detecting the binding of the compound to amyloid deposit in the subject.

30. The method according to claim 29, wherein said detection is carried out by gamma imaging, magnetic resonance imaging, or magnetic resonance spectroscopy.

31. The method according to claim 29, wherein the subject is suspected of having a disease or syndrome selected from the group consisting of Alzheimer's Disease, familial Alzheimer's Disease, Down's Syndromes and homozygotes for the apolipoprotein E4 allele.

* * * * *